(12) United States Patent
Jang et al.

(10) Patent No.: US 10,832,552 B2
(45) Date of Patent: Nov. 10, 2020

(54) ELECTRONIC DEVICE AND METHOD FOR PROVIDING NOTIFICATION USING SAME

(71) Applicant: Samsung Electronics Co., Ltd., Gyeonggi-do (KR)

(72) Inventors: Jihoon Jang, Gyeonggi-do (KR); Duseok Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/469,291

(22) PCT Filed: Dec. 14, 2017

(86) PCT No.: PCT/KR2017/014714
§ 371 (c)(1),
(2) Date: Jun. 13, 2019

(87) PCT Pub. No.: WO2018/110996
PCT Pub. Date: Jun. 21, 2018

(65) Prior Publication Data
US 2020/0105116 A1    Apr. 2, 2020

(30) Foreign Application Priority Data
Dec. 16, 2016 (KR) .......................... 10-2016-0172367

(51) Int. Cl.
*G08B 21/04* (2006.01)
*H04W 4/029* (2018.01)

(52) U.S. Cl.
CPC ..... *G08B 21/0423* (2013.01); *G08B 21/0453* (2013.01); *H04W 4/029* (2018.02)

(58) Field of Classification Search
CPC  G08B 21/0423; G08B 21/0453; H04W 4/029
(Continued)

(56) References Cited

U.S. PATENT DOCUMENTS 5,959,529 A  *  9/1999  Kail, IV ................. G01S 19/17
                                                   340/539.12
8,786,425 B1 *  7/2014  Hutz ........................ G08B 1/08
                                                   340/526

(Continued)

FOREIGN PATENT DOCUMENTS

JP      5416474 B2    11/2013
JP      5490490 B2     3/2014
(Continued)

*Primary Examiner* — Daryl C Pope
(74) *Attorney, Agent, or Firm* — Cha & Reiter, LLC

(57) ABSTRACT

The present invention relates to an electronic device and a method for providing a notification using the same. An electronic device according to various embodiments of the present invention may comprise: a wireless communication unit; a sensor unit; a memory; and a processor electrically connected to the wireless communication unit, the sensor unit, and the memory, wherein the memory includes instructions which, when executed, cause the processor to: collect situation information of the electronic device and sensor information obtained by the sensor unit; analyze a pattern on the basis of the situation information and the sensor information; and transmit information on the analyzed pattern to a designated external electronic device through the wireless communication unit.

10 Claims, 19 Drawing Sheets

(58) Field of Classification Search
USPC .............................. 340/539.11, 539.1, 539.13
See application file for complete search history.

(56) References Cited

U.S. PATENT DOCUMENTS

| | | |
|---|---|---|
| 2007/0241888 A1 | 10/2007 | Mantovani et al. |
| 2013/0321157 A1 | 12/2013 | Takamura et al. |
| 2014/0312934 A1 | 10/2014 | Motz |
| 2015/0348389 A1 | 12/2015 | Jang et al. |
| 2016/0058366 A1 | 3/2016 | Choi et al. |
| 2016/0287142 A1 | 10/2016 | Han et al. |

FOREIGN PATENT DOCUMENTS

| | | |
|---|---|---|
| JP | 5935516 B2 | 5/2016 |
| KR | 10-2014-0119571 A | 10/2014 |
| KR | 10-2015-0136716 A | 12/2015 |
| KR | 10-2016-0024627 A | 3/2016 |
| KR | 10-2016-0119612 A | 10/2016 |
| KR | 10-2016-0136906 A | 11/2016 |

* cited by examiner

User Location clustering

Hierarchical location modeling

Semantic Annotation

ELECTRONIC DEVICE AND METHOD FOR PROVIDING NOTIFICATION USING SAME

CROSS REFERENCE TO RELATED APPLICATIONS

This application is a National Phase Entry of PCT International Application No. PCT/KR2017/014714, which was filed on Dec. 14, 2017, and claims a priority to Korean Patent Application No. 10-2016-0172367, which was filed on Dec. 16, 2016, the contents of which are incorporated herein by reference.

TECHNICAL FIELD

Various embodiments of the disclosure relate to a method and an electronic device capable of analyzing behavior patterns of a user using the electronic device and providing a notification based on the analyzed behavior patterns.

BACKGROUND ART

In general, an electronic device is provided with various sensors. Using such various sensors, the electronic device can monitor user's behaviors in real time. In particular, if an emergency situation occurs to an old person who has a high probability of getting into the emergency situation and a low emergency response capability, prompt coping with the emergency situation is required, and thus technology to monitor the behaviors of an old person becomes essential.

DISCLOSURE OF INVENTION

Technical Problem

However, an electronic device only monitors user's activities in real time, but it does not analyze user's patterns based on monitoring information to provide a corresponding notification. Further, in the case where an emergency situation occurs, a user may ask for rescue by directly pressing a button separately provided. However, if a user is in an unconsciousness state, prompt coping is not possible. Further, a user may additionally install a sensor in a space where the user is frequently located, but this may cause additional costs to occur.

An electronic device according to various embodiments of the disclosure can monitor user's movement using various sensors provided therein, and it can collect sensor information on the movement and location information in accordance with time. The electronic device can manage the user's patterns based on the collected sensor information and the location information in accordance with time. The electronic device can automatically transmits notification information on the analyzed patterns to an external electronic device.

Solution to Problem

According to various embodiments of the disclosure, an electronic device includes a wireless communication circuitry; a sensor circuitry; a memory; and a processor electrically connected to the wireless communication circuitry, the sensor circuitry, and the memory, wherein the memory, when executed, includes instructions to cause the processor to collect situation information of the electronic device and sensor information through the sensor circuitry, to analyze a pattern based on the situation information and the sensor information, and to transmit information on the analyzed pattern to a designated external electronic device through the wireless communication circuitry.

According to various embodiments of the disclosure, a method for providing a notification using an electronic device includes collecting situation information of the electronic device and sensor information; and analyzing a pattern based on the situation information and the sensor information, and transmitting information on the analyzed pattern to a designated external electronic device.

Advantageous Effects of Invention

The electronic device according to various embodiments of the disclosure can predict a main life pattern of a user through management of user's movement pattern. Because the electronic device can predict the main life pattern and it can automatically transmit notification information on the patterns to the external electronic device, it is possible to support proper responses and services in accordance with various situations.

The electronic device according to various embodiments of the disclosure can collect the location information with low power consumption in a predetermined condition, and thus power consumption of the electronic device can be reduced.

MODE FOR THE INVENTION

Figure 1:
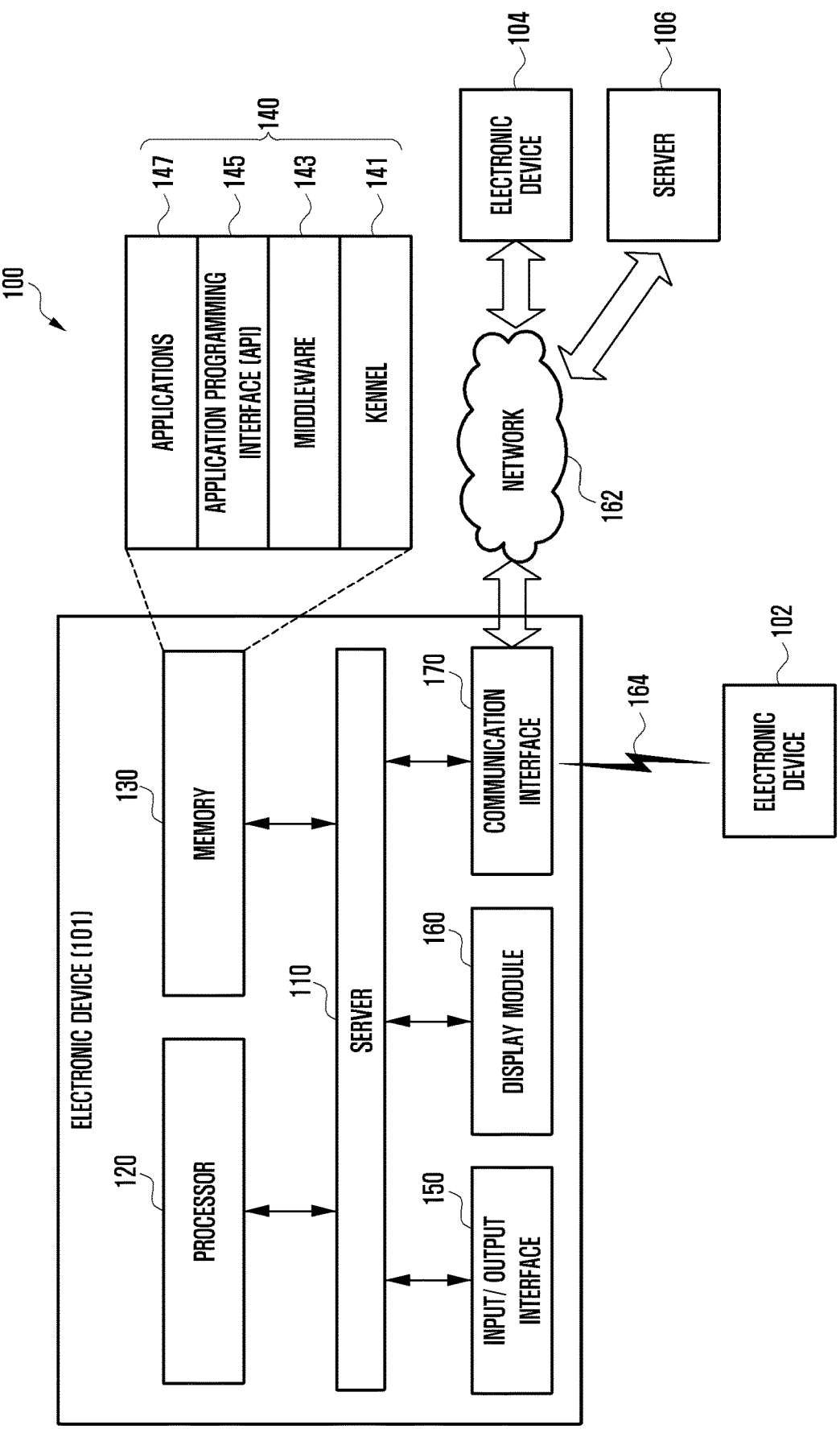
FIG. 1 is a diagram illustrating an electronic device in a network environment according various embodiments of the disclosure.

Hereinafter, various embodiments of the present disclosure may be described with reference to accompanying drawings. Accordingly, those of ordinary skill in the art will recognize that modification, equivalent, and/or alternative on the various embodiments described herein can be variously made without departing from the scope and spirit of the present disclosure.

With regard to description of drawings, similar elements may be marked by similar reference numerals. The terms of a singular form may include plural forms unless otherwise specified.

In this disclosure, the expressions "A or B", "at least one of A or/and B", or "one or more of A or/and B", and the like may include any and all combinations of one or more of the associated listed items.

The terms, such as "first", "second", and the like may be used to refer to various elements regardless of the order and/or the priority and to distinguish the relevant elements from other elements, but do not limit the elements.

When an element (e.g., a first element) is referred to as being "(operatively or communicatively) coupled with/to" or "connected to" another element (e.g., a second element), the element may be directly coupled with/to or connected to the other element or an intervening element (e.g., a third element) may be present.

According to the situation, the expression "configured to" used in this disclosure may be used as, for example, the expression "suitable for", "having the capacity to", "adapted to", "made to", "capable of", or "designed to" in hardware or software. The expression "a device configured to" may mean that the device is "capable of" operating together with another device or other components.

For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

An electronic device according to various embodiments of this disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, medical devices, cameras, or wearable devices. According to various embodiments, the wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit).

According to various embodiments, the electronic device may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, media boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, drones, automatic teller's machines (ATMs), points of sales (POSs) of stores, or internet of things (e.g., light bulbs, various sensors, sprinkler devices, fire alarms, thermostats, street lamps, toasters, exercise equipment, hot water tanks, heaters, boilers, and the like).

According to an embodiment, the electronic device may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be a flexible electronic device or a combination of two or more above-described devices.

Furthermore, an electronic device according to an embodiment of this disclosure may not be limited to the above-described electronic devices. In this disclosure, the term "user" may refer to a person who uses an electronic device or may refer to a device (e.g., an artificial intelligence electronic device) that uses the electronic device.

Referring to FIG. 1, according to various embodiments, an electronic device 101 in a network environment is described. The electronic device 101 may include a bus 110, a processor 120, a memory 130, an input/output interface 150, a display 160, and a communication interface 170. According to an embodiment, the electronic device 101 may not include at least one of the above-described elements or may further include other element(s). The bus 110 may interconnect the above-described elements 110 to 170 and may include a circuit for conveying communications (e.g., a control message and/or data) among the above-described elements. The processor 120 may include one or more of a central processing unit (CPU), an application processor (AP), or a communication processor (CP). For example, the processor 120 may perform an arithmetic operation or data processing associated with control and/or communication of at least other elements of the electronic device 101.

The memory 130 may include a volatile and/or nonvolatile memory. For example, the memory 130 may store instructions or data associated with at least one other element(s) of the electronic device 101. According to an embodiment, the memory 130 may store software and/or a program 140. The program 140 may include, for example, a kernel 141, a middleware 143, an application programming interface (API) 145, and/or an application program (or "an application") 147. At least a part of the kernel 141, the middleware 143, or the API 145 may be referred to as an "operating system (OS)". For example, the kernel 141 may control or manage system resources (e.g., the bus 110, the processor 120, the memory 130, and the like) that are used to execute operations or functions of other programs (e.g., the middleware 143, the API 145, and the application program 147). Furthermore, the kernel 141 may provide an interface that allows the middleware 143, the API 145, or the application program 147 to access discrete elements of the electronic device 101 so as to control or manage system resources.

The middleware 143 may perform, for example, a mediation role such that the API 145 or the application program 147 communicates with the kernel 141 to exchange data. Furthermore, the middleware 143 may process one or more task requests received from the application program 147 according to a priority. For example, the middleware 143 may assign the priority, which makes it possible to use a system resource (e.g., the bus 110, the processor 120, the memory 130, or the like) of the electronic device 101, to at least one of the application program 147 and may process the one or more task requests. The API 145 may be an interface through which the application program 147 controls a function provided by the kernel 141 or the middleware 143, and may include, for example, at least one interface or function (e.g., a command or an instruction) for a file control, a window control, image processing, a character control, or the like. The input/output interface 150 may transmit an instruction or data input from a user or another external device, to other element(s) of the electronic device 101 or may output an instruction or data, received from other element(s) of the electronic device 101, to a user or another external device.

The display 160 may include, for example, a liquid crystal display (LCD), a light-emitting diode (LED) display, an organic LED (OLED) display, a microelectromechanical systems (MEMS) display, or an electronic paper display. The display 160 may display, for example, various contents (e.g., a text, an image, a video, an icon, a symbol, and the like) to a user. The display 160 may include a touch screen and may receive, for example, a touch, gesture, proximity, or hovering input using an electronic pen or a part of a user's body. For example, the communication interface 170 may establish communication between the electronic device 101 and an external device (e.g., the first electronic device 102, the second electronic device 104, or the server 106). For example, the communication interface 170 may be connected to the network 162 over wireless communication or wired communication to communicate with the external device (e.g., the second electronic device 104 or the server 106).

For example, the wireless communication may include cellular communication using at least one of long-term evolution (LTE), LTE Advanced (LTE-A), Code Division Multiple Access (CDMA), Wideband CDMA (WCDMA), Universal Mobile Telecommunications System (UMTS), Wireless Broadband (WiBro), Global System for Mobile Communications (GSM), or the like. The wireless communication may include at least one of wireless fidelity (Wi-Fi), Bluetooth, Bluetooth low energy (BLE), Zigbee, near field communication (NFC), magnetic stripe transmission (MST), radio frequency (RF), a body area network, or the like. According to an embodiment, the wireless communication may include GNSS. The GNSS may be one of, for example, a global positioning system (GPS), a global navigation satellite system (Glonass), a Beidou navigation satellite system (hereinafter referred to as "Beidou"), or an European global satellite-based navigation system (hereinafter referred to as "Galileo"). Hereinafter, in this disclosure, "GPS" and "GNSS" may be interchangeably used. The wired communication may include at least one of, for example, a universal serial bus (USB), a high definition multimedia interface (HDMI), a recommended standard-232 (RS-232), power line communication, a plain old telephone service (POTS), or the like. The network 162 may include at least one of telecommunications networks, for example, a computer network (e.g., LAN or WAN), an Internet, or a telephone network.

Each of the first and second external electronic devices 102 and 104 may be a device of which the type is different from or the same as that of the electronic device 101. According to various embodiments, all or a portion of operations that the electronic device 101 will perform may be executed by another or plural electronic devices (e.g., the first electronic device 102, the second electronic device 104 or the server 106). According to an embodiment, in the case where the electronic device 101 executes any function or service automatically or in response to a request, the electronic device 101 may not perform the function or the service internally, but, alternatively additionally, it may request at least a portion of a function associated with the electronic device 101 at other electronic device (e.g., the electronic device 102 or 104 or the server 106). The other electronic device (e.g., the electronic device 102 or 104 or the server 106) may execute the requested function or additional function and may transmit the execution result to the electronic device 101. The electronic device 101 may provide the requested function or service using the received result or may additionally process the received result to provide the requested function or service. To this end, for example, cloud computing, distributed computing, or client-server computing may be used.

Figure 2:
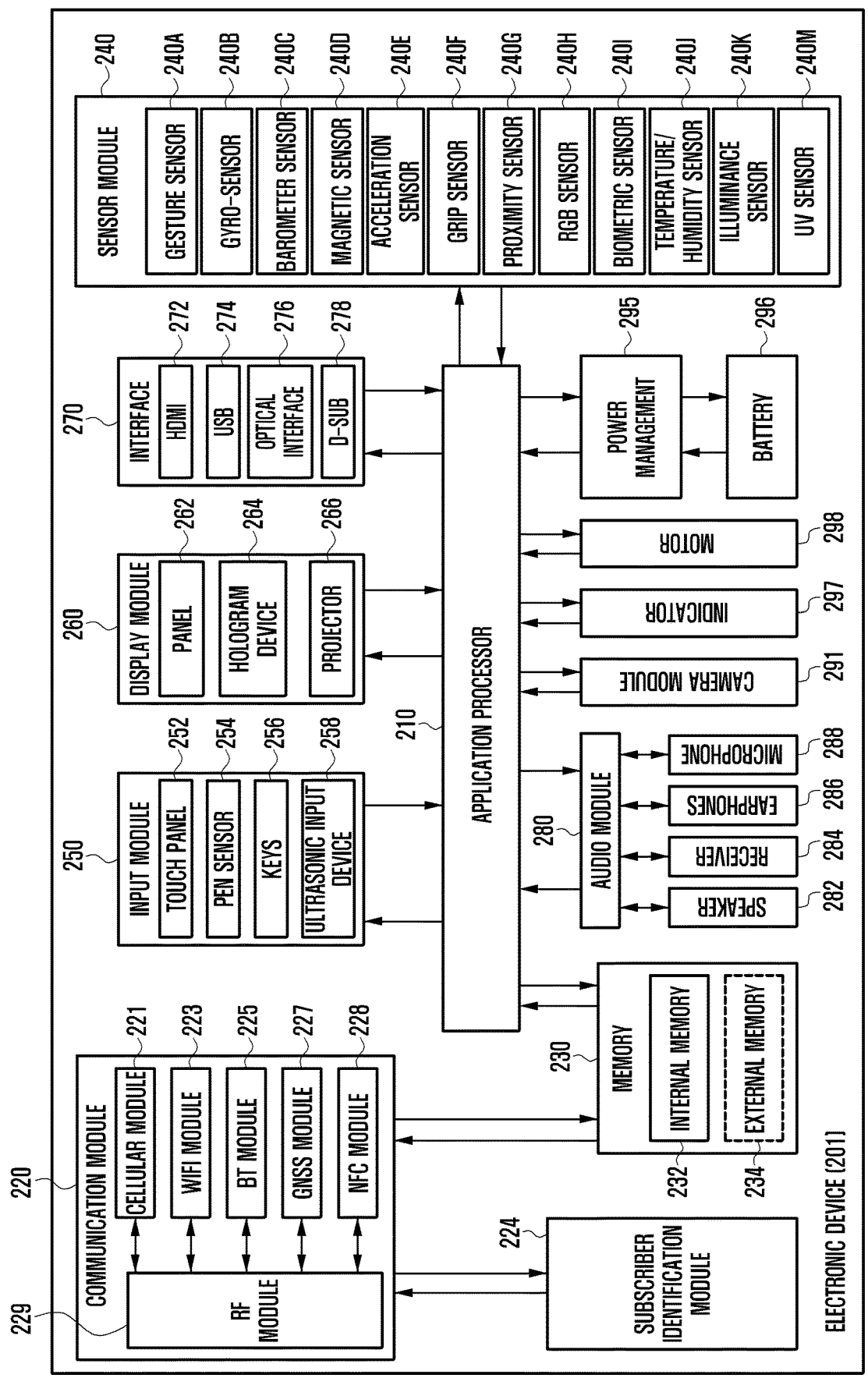
FIG. 2 is a block diagram of an electronic device according to various embodiments of the disclosure.

FIG. 2 illustrates a block diagram of an electronic device, according to various embodiments.

An electronic device 201 may include, for example, all or a part of the electronic device 101 illustrated in FIG. 1. The electronic device 201 may include one or more processors (e.g., an application processor (AP)) 210, a communication module 220, a subscriber identification module 224, a memory 230, a sensor module 240, an input device 250, a display module 260, an interface 270, an audio module 280, a camera module 291, a power management module 295, a battery 296, an indicator 297, and a motor 298. For example, the processor 210 may be implemented with a System on Chip (SoC). According to an embodiment, the processor 210 may further include a graphic processing unit (GPU) and/or an image signal processor. The processor 210 may include at least a part (e.g., a cellular module 221) of elements illustrated in FIG. 2. The processor 210 may load an instruction or data, which is received from at least one of other elements (e.g., a nonvolatile memory), into a volatile memory and process the loaded instruction or data. The processor 210 may store result data in the nonvolatile memory.

The communication module 220 may be configured the same as or similar to the communication interface 170 of FIG. 1. The communication module 220 may include the cellular module 221, a Wi-Fi module 223, a Bluetooth (BT) module 225, a GNSS module 227, a near field communication (NFC) module 228, and a radio frequency (RF) module 229. The cellular module 221 may provide, for example, voice communication, video communication, a character service, an Internet service, or the like over a communication network. According to an embodiment, the cellular module 221 may perform discrimination and authentication of the electronic device 201 within a communication network by using the subscriber identification module (e.g., a SIM card) 224. According to an embodiment, the cellular module 221 may perform at least a portion of functions that the processor 210 provides. According to an embodiment, the cellular module 221 may include a communication processor (CP). According to an embodiment, at least a part (e.g., two or more) of the cellular module 221, the Wi-Fi module 223, the BT module 225, the GNSS module 227, or the NFC module 228 may be included within one Integrated Circuit (IC) or an IC package. For example, the RF module 229 may transmit and receive a communication signal (e.g., an RF signal). For example, the RF module 229 may include a transceiver, a power amplifier module (PAM), a frequency filter, a low noise amplifier (LNA), an antenna, or the like. According to another embodiment, at least one of the cellular module 221, the Wi-Fi module 223, the BT module 225, the GNSS module 227, or the NFC module 228 may transmit and receive an RF signal through a separate RF module. The subscriber identification module 224 may include, for example, a card and/or embedded SIM that includes a subscriber identification module and may include unique identify information (e.g., integrated circuit card identifier (ICCID)) or subscriber information (e.g., international mobile subscriber identity (IMSI)).

The memory 230 (e.g., the memory 130) may include an internal memory 232 or an external memory 234. For example, the internal memory 232 may include at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory, a hard drive, or a solid state drive (SSD). The external memory 234 may include a flash drive such as compact flash (CF), secure digital (SD), micro secure digital (Micro-SD), mini secure digital (Mini-SD), extreme digital (xD), a multimedia card (MMC), a memory stick, or the like. The external memory 234 may be operatively and/or physically connected to the electronic device 201 through various interfaces.

The sensor module 240 may measure, for example, a physical quantity or may detect an operation state of the electronic device 201. The sensor module 240 may convert the measured or detected information to an electric signal. For example, the sensor module 240 may include at least one of a gesture sensor 240A, a gyro sensor 240B, a barometric pressure sensor 240C, a magnetic sensor 240D, an acceleration sensor 240E, a grip sensor 240F, the proximity sensor 240G, a color sensor 240H (e.g., red, green, blue (RGB) sensor), a biometric sensor 240I, a temperature/humidity sensor 240J, an illuminance sensor 240K, or an UV sensor 240M. Although not illustrated, additionally or generally, the sensor module 240 may further include, for example, an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling at least one or more sensors included therein. According to an embodiment, the electronic device 201 may further include a processor that is a part of the processor 210 or independent of the processor 210 and is configured to control the sensor module 240. The processor may control the sensor module 240 while the processor 210 remains at a sleep state.

The input device 250 may include, for example, a touch panel 252, a (digital) pen sensor 254, a key 256, or an ultrasonic input unit 258. For example, the touch panel 252 may use at least one of capacitive, resistive, infrared and ultrasonic detecting methods. Also, the touch panel 252 may further include a control circuit. The touch panel 252 may further include a tactile layer to provide a tactile reaction to a user. The (digital) pen sensor 254 may be, for example, a part of a touch panel or may include an additional sheet for recognition. The key 256 may include, for example, a physical button, an optical key, or a keypad. The ultrasonic input device 258 may detect (or sense) an ultrasonic signal, which is generated from an input device, through a microphone (e.g., a microphone 288) and may check data corresponding to the detected ultrasonic signal.

The display module 260 (e.g., the display 160) may include a panel 262, a hologram device 264, a projector 266, and/or a control circuit for controlling the panel 262, the hologram device 264, or the projector 266. The panel 262 may be implemented, for example, to be flexible, transparent or wearable. The panel 262 and the touch panel 252 may be integrated into a single module. According to an embodiment, the panel 262 may include a pressure sensor (or force sensor) that measures the intensity of touch pressure by a user. The pressure sensor may be implemented integrally with the touch panel 252, or may be implemented as at least one sensor separately from the touch panel 252. The hologram device 264 may display a stereoscopic image in a space using a light interference phenomenon. The projector 266 may project light onto a screen so as to display an image. For example, the screen may be arranged in the inside or the outside of the electronic device 201. The interface 270 may include, for example, a high-definition multimedia interface (HDMI) 272, a universal serial bus (USB) 274, an optical interface 276, or a D-subminiature (D-sub) 278. The interface 270 may be included, for example, in the communication interface 170 illustrated in FIG. 1. Additionally or generally, the interface 270 may include, for example, a mobile high definition link (MHL) interface, a SD card/multi-media card (MMC) interface, or an infrared data association (IrDA) standard interface.

The audio module 280 may convert a sound and an electric signal in dual directions. At least a part of the audio module 280 may be included, for example, in the input/output interface 150 illustrated in FIG. 1. The audio module 280 may process, for example, sound information that is input or output through a speaker 282, a receiver 284, an earphone 286, or the microphone 288. For example, the camera module 291 may shoot a still image or a video. According to an embodiment, the camera module 291 may include at least one or more image sensors (e.g., a front sensor or a rear sensor), a lens, an image signal processor (ISP), or a flash (e.g., an LED or a xenon lamp). The power management module 295 may manage, for example, power of the electronic device 201. According to an embodiment, a power management integrated circuit (PMIC), a charger IC, or a battery or fuel gauge may be included in the power management module 295. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, a rectifier, or the like. The battery gauge may measure, for example, a remaining capacity of the battery 296 and a voltage, current or temperature thereof while the battery is charged. The battery 296 may include, for example, a rechargeable battery and/or a solar battery.

The indicator 297 may display a specific state of the electronic device 201 or a part thereof (e.g., the processor 210), such as a booting state, a message state, a charging state, and the like. The motor 298 may convert an electrical signal into a mechanical vibration and may generate the following effects: vibration, haptic, and the like. The electronic device 201 may include a processing device (e.g., a GPU) for supporting a mobile TV. The processing device for supporting the mobile TV may process media data according to the standards of digital multimedia broadcasting (DMB), digital video broadcasting (DVB), MediaFLO™, or the like. Each of the above-mentioned elements of the electronic device according to various embodiments of the present disclosure may be configured with one or more components, and the names of the elements may be changed according to the type of the electronic device. In various embodiments, some elements of the electronic device (e.g., the electronic device 201) may be omitted or other additional elements may be added. Furthermore, some of the elements of the electronic device may be combined with each other so as to form one entity, so that the functions of the elements may be performed in the same manner as before the combination.

Figure 3:
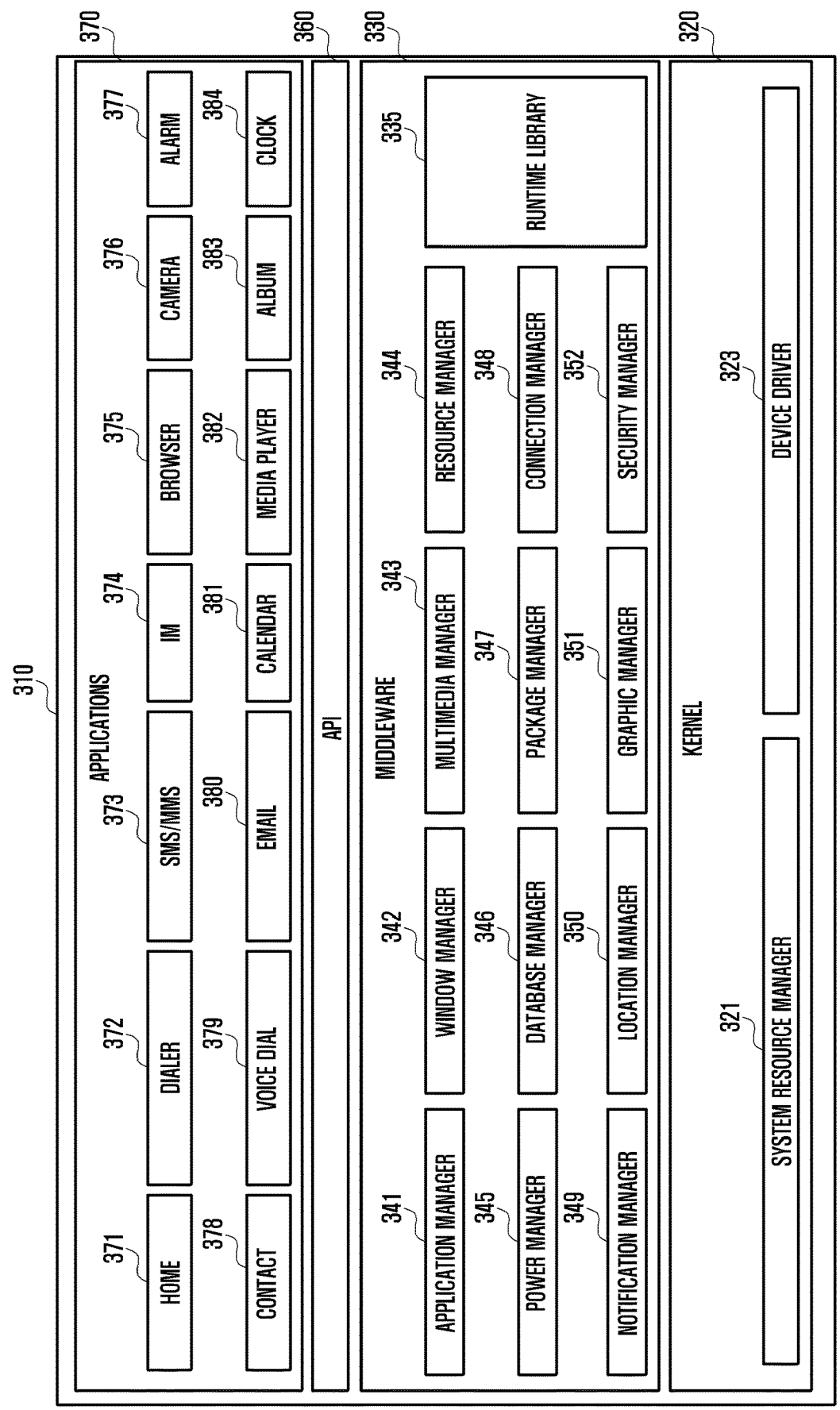
FIG. 3 is a block diagram of a program module according to various embodiment of the disclosure.

FIG. 3 illustrates a block diagram of a program module, according to various embodiments.

According to an embodiment, a program module 310 (e.g., the program 140) may include an operating system (OS) to control resources associated with an electronic device (e.g., the electronic device 101), and/or diverse applications (e.g., the application program 147) driven on the OS. The OS may be, for example, Android™, iOS™, Windows™, Symbian™, Tizen™, or Bada™. The program module 310 may include a kernel 320 (e.g., the kernel 141), a middleware 330 (e.g., the middleware 143), an application programming interface (API) 360 (e.g., the API 145), and/or an application 370 (e.g., the application program 147). At least a portion of the program module 310 may be preloaded on an electronic device or may be downloadable from an external electronic device (e.g., the first electronic device 102, the second electronic device 104, the server 106, or the like).

The kernel 320 (e.g., the kernel 141) may include, for example, a system resource manager 321 or a device driver 323. The system resource manager 321 may control, allocate, or retrieve system resources. According to an embodiment, the system resource manager 321 may include a process managing unit, a memory managing unit, a file system managing unit, or the like. The device driver 323 may include, for example, a display driver, a camera driver, a Bluetooth driver, a shared memory driver, a USB driver, a keypad driver, a Wi-Fi driver, an audio driver, or an interprocess communication (IPC) driver. The middleware 330 may provide, for example, a function that the application 370 needs in common, or may provide diverse functions to the application 370 through the API 360 to allow the application 370 to efficiently use limited system resources of the electronic device. According to an embodiment, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include, for example, a library module that is used by a compiler to add a new function through a programming language while the application 370 is being executed. The runtime library 335 may perform input/output management, memory management, or capacities about arithmetic functions. The application manager 341 may manage, for example, a life cycle of at least one application of the application 370. The window manager 342 may manage a graphic user interface (GUI) resource that is used in a screen. The multimedia manager 343 may identify a format necessary for playing diverse media files, and may perform encoding or decoding of media files by using a codec suitable for the format. The resource manager 344 may manage resources such as a memory space or source code of the application 370. The power manager 345 may manage a battery or power, and may provide power information for an operation of an electronic device. According to an embodiment, the power manager 345 may operate with a basic input/output system (BIOS). The database manager 346 may generate, search for, or modify database that is to be used in the application 370. The package manager 347 may install or update an application that is distributed in the form of package file.

The connectivity manager 348 may manage, for example, wireless connection. The notification manager 349 may provide an event, for example, arrival message, appointment, or proximity notification to a user. For example, the location manager 350 may manage location information about an electronic device. The graphic manager 351 may manage a graphic effect that is provided to a user, or manage a user interface relevant thereto. The security manager 352 may provide, for example, system security or user authentication. According to an embodiment, the middleware 330 may include a telephony manager for managing a voice or video call function of the electronic device or a middleware module that combines diverse functions of the above-described elements. According to an embodiment, the middleware 330 may provide a module specialized to each OS kind to provide differentiated functions. Additionally, the middleware 330 may dynamically remove a part of the preexisting elements or may add new elements thereto. The API 360 may be, for example, a set of programming functions and may be provided with a configuration that is variable depending on an OS. For example, in the case where an OS is the android or the iOS, it may provide one API set per platform. In the case where an OS is the tizen, it may provide two or more API sets per platform.

The application 370 may include, for example, applications such as a home 371, a dialer 372, an SMS/MMS 373, an instant message (IM) 374, a browser 375, a camera 376, an alarm 377, a contact 378, a voice dial 379, an e-mail 380, a calendar 381, a media player 382, an album 383, a watch 384, health care (e.g., measuring an exercise quantity, blood sugar, or the like) or offering of environment information (e.g., information of barometric pressure, humidity, temperature, or the like). According to an embodiment, the application 370 may include an information exchanging application to support information exchange between an electronic device and an external electronic device. The information exchanging application may include, for example, a notification relay application for transmitting specific information to an external electronic device, or a device management application for managing the external electronic device. For example, the notification relay application may include a function of transmitting notification information, which arise from other applications, to an external electronic device or may receive, for example, notification information from an external electronic device and provide the notification information to a user. The device management application may install, delete, or update for example, a function (e.g., turn-on/turn-off of an external electronic device itself (or a part of components) or adjustment of brightness (or resolution) of a display) of the external electronic device which communicates with the electronic device, and an application running in the external electronic device. According to an embodiment, the application 370 may include an application (e.g., a health care application of a mobile medical device) that is assigned in accordance with an attribute of an external electronic device. According to an embodiment, the application 370 may include an application that is received from an external electronic device. At least a portion of the program module 310 may be implemented by software, firmware, hardware (e.g., the processor 210), or a combination (e.g., execution) of two or more thereof, and may include modules, programs, routines, sets of instructions, processes, or the like for performing one or more functions.

The "module" used in this document may include a unit including hardware, software or firmware and may be interchangeably used with a term, for example, logic, a logical block, a part or a circuit. The "module" may be an integrated part, a minimum unit to perform one or more functions, or a part thereof. The "module" may be implemented mechanically or electronically, and may include an application-specific integrated circuit (ASIC) chip, field-programmable gate arrays (FPGAs) or a programmable logic device which performs some operations and which has been known or is to be developed, for example. At least some of a device (e.g., modules or functions thereof) or method (e.g., operations) according to various embodiments may be implemented as instructions stored in a computer-readable storage medium (e.g., the memory 130) in the form of a program module. If the instructions are executed by a processor (e.g., the processor 120), the processor may perform functions corresponding to the instructions. The computer-readable storage medium may include a hard disk, a floppy disk, magnetic media (e.g., magnetic tape), optical media (e.g., CD-ROM), a DVD, magneto-optical media (e.g., a floptical disk), and embedded memory. The instructions may include code generated by a compiler or code executable by an interpreter. The module or program module according to various embodiments may include at least one of the aforementioned elements, may omit some of the elements or may further include other elements. Operations performed by the module, program module or other elements according to various embodiments may be executed in a sequential, parallel, repetitive or heuristic manner or at least some operations may be executed in a different sequence or omitted or may further include other operations.

Figure 4:
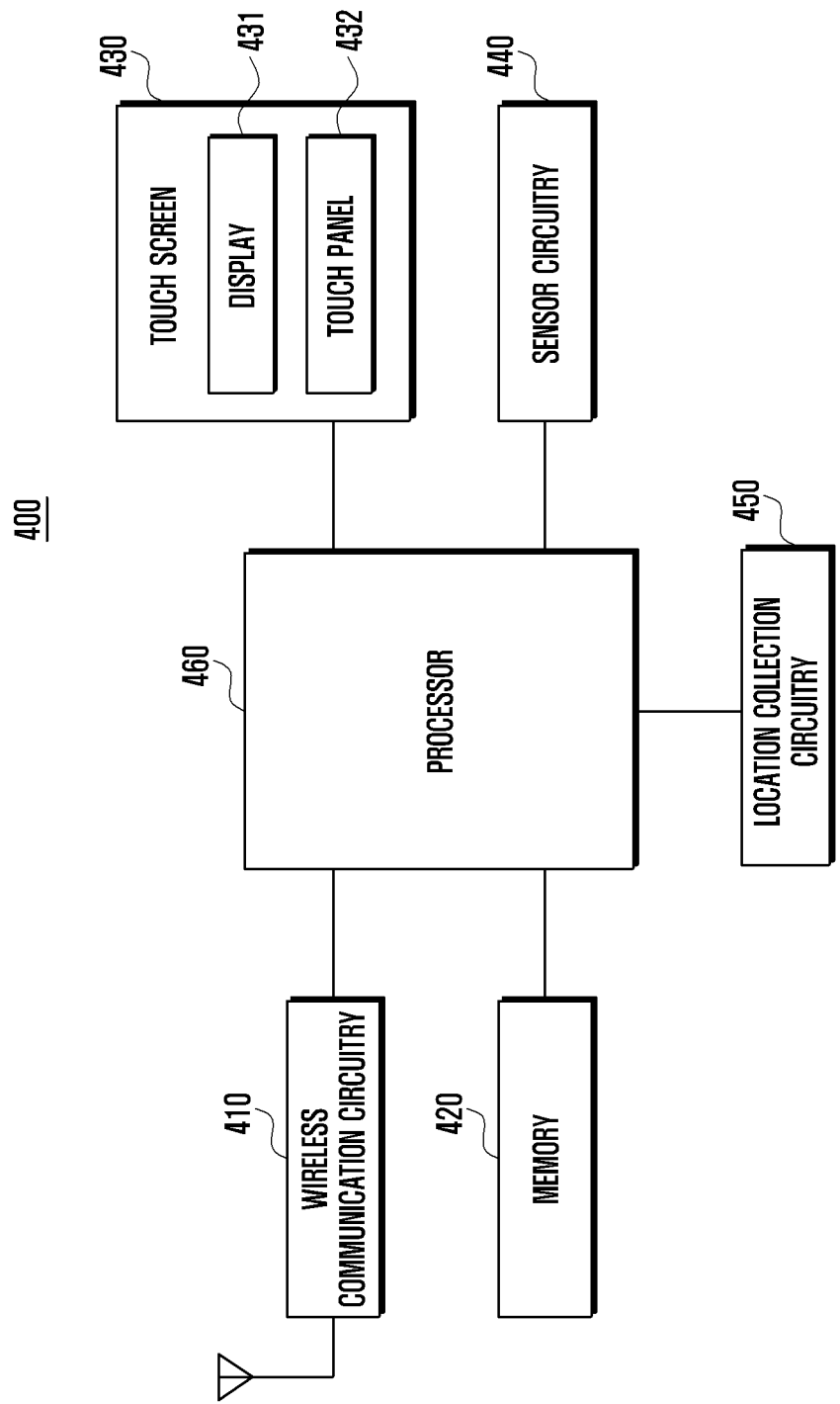
FIG. 4 is a block diagram of an electronic device according to various embodiments of the disclosure.

FIG. 4 is a block diagram of an electronic device according to various embodiments of the disclosure.

With reference to FIG. 4, an electronic device 400 (e.g., electronic device 101 of FIG. 1) may include a wireless communication circuitry 410, a memory 420, a touch screen 430, a sensor circuitry 440, a location collection circuitry 450, and a processor 460.

According to various embodiments of the disclosure, the wireless communication circuitry 410 (e.g., communication interface 170 of FIG. 1 or communication module 220 of FIG. 2) can connect a communication between the electronic device 400 and an external electronic device (e.g., electronic device 102, electronic device 104, or server 106 of FIG. 1).

According to various embodiments of the disclosure, the memory 420 (e.g., memory 130 of FIG. 1 or memory 230 of FIG. 2) may map and store therein location information of the electronic device 400 and time information on a time when the location information is collected. The memory 420 may store therein sensor signals for determining user's behaviors, for example, user's motion information (e.g., walking, running, stop, and fall) and user's movement information using movement means (vehicle, bicycle, subway, elevator, escalator, and stairs).

According to various embodiments of the disclosure, the memory 420 may store therein a movement pattern of the electronic device 400. The pattern may include at least one of a place in which the electronic device 400 is located in accordance with a time, a place movement order, a time for which the electronic device 400 stays in one place, an average movement start time in the case of moving to another place, an average movement end time, an average movement consumption time, and a movement means used in the case of the movement.

According to various embodiments of the disclosure, the memory 420 may store therein a vibration pattern in accordance with vehicle driving in order to determine whether to drive a vehicle.

According to various embodiments of the disclosure, the memory 420 may store therein a strongpoint recognized based on the movement pattern of the electronic device 400.

According to various embodiments of the disclosure, the memory 420 may store therein a condition for collecting the location information with low power consumption.

According to various embodiments of the disclosure, the touch screen 430 may be integrally configured to include a display 431 (e.g., display 160 of FIG. 1 or display 260 of FIG. 2) and a touch panel 433 (e.g., input device 250 of FIG. 2).

According to various embodiments of the disclosure, the touch screen 430 may display a screen in accordance with the function performance of the electronic device 400 under the control of the processor 460. For example, under the control of the processor 460, the touch screen 430 may display a user interface for configuring a specific strongpoint and a user interface for providing the corresponding service if the user's location is the strongpoint. Further, the touch screen 430 may display a user interface for designating an external electronic device that will transmit information on the analyzed pattern.

According to various embodiments of the disclosure, the sensor circuitry 440 (e.g., sensor module 240 of FIG. 2) may include at least one of a motion sensor, a gyro sensor, a magnetic sensor, and an acceleration sensor.

According to various embodiments of the disclosure, the motion sensor, the gyro sensor, and the acceleration sensor may detect the motion of the electronic device 400. The sensor circuitry 440 may transmit sensor information in accordance with the detected movement of the electronic device 400 to the processor 460.

According to various embodiments of the disclosure, the magnetic sensor may identify the direction of the electronic device 400.

According to various embodiments of the disclosure, the location collection circuitry 450 may include at least one of a network location provider (NLP), a GPS, a cell location, and a passive provider. The location collection circuitry 450 may acquire location information of the electronic device 400 in response to a request for acquiring the location information of the electronic device 400.

According to various embodiments of the disclosure, the location collection circuitry 450 may operate with low power consumption. If the state of the electronic device 400 satisfies a condition for collecting the location information with low power consumption, the location collection circuitry 450 may operate with low power consumption under the control of the processor 460.

According to various embodiments of the disclosure, the processor 460 (e.g., processor 210 of FIG. 2) may control the overall operation of the electronic device 400 and a signal flow between internal constituent elements of the electronic device 400, perform data processing, and control power supply from the battery to the above-described constituent elements.

According to various embodiments of the disclosure, the processor 460 may collect situation information including location information of the electronic device 400 and time information on a time when the location information is acquired.

According to various embodiments of the disclosure, if the condition for collecting the location information with low power consumption is satisfied, the processor 460 may control the location collection circuitry 450 to operate with low power consumption. The condition for collecting the location information with low power consumption may include at least one of whether the electronic device 400 is located in a specific strongpoint, whether the pattern of the electronic device 400 is a stop state pattern, and whether a difference between the time when the location information was previously collected and the current time is included in a predetermined value.

For example, according to various embodiments of the disclosure, if the situation information of the electronic device 400 coincides with the situation information stored in the memory 420 (e.g., if the spot where the electronic device is located at a specific time is the strongpoint), the processor 460 may activate a mode in which the location information is collected with low power consumption.

According to various embodiments of the disclosure, the processor 460 may receive sensor information in accordance with the movement of the electronic device 400 through the sensor circuitry 440. If it is recognized that the electronic device 400 is in a stop state based on the received sensor information, and the stop state is maintained for a predetermined time, the processor 460 may activate the mode in which the location information is collected with low power consumption.

According to various embodiments of the disclosure, if a request for collection of the location information of the electronic device 400 is detected, the processor 460 may compare the time when the location information was previously collected with the current time. If the time difference is included in the predetermined value as the result of the comparison (e.g., if the time difference is within 10 minutes), the processor 460 may use the previously collected location information.

According to various embodiments of the disclosure, the processor 460 may request a first location collection circuitry (e.g., network provider) having low power consumption to provide the location information of the electronic device 400. If the location information collected by the first location collection circuitry is not included in a predetermined range, the processor 460 may request a second location collection circuitry (e.g., GPS) having higher power consumption than the power consumption of the first location collection circuitry to provide the location information of the electronic device 400.

According to various embodiments of the disclosure, the processor 460 may collect a sensor signal received by the sensor circuitry 440, and based on this, it may determine the behavior of a user (e.g., user's motion information or user's movement information using a movement means).

According to various embodiments of the disclosure, the processor 460 may analyze a pattern based on the collected situation information and sensor information, and it may compare the analyzed pattern with a pre-stored pattern. If the analyzed pattern is different from the pre-stored pattern as the result of the comparison, the processor 460 may transmit notification information generated based on the sensor information and the situation information to a predesignated external electronic device.

Figure 5:
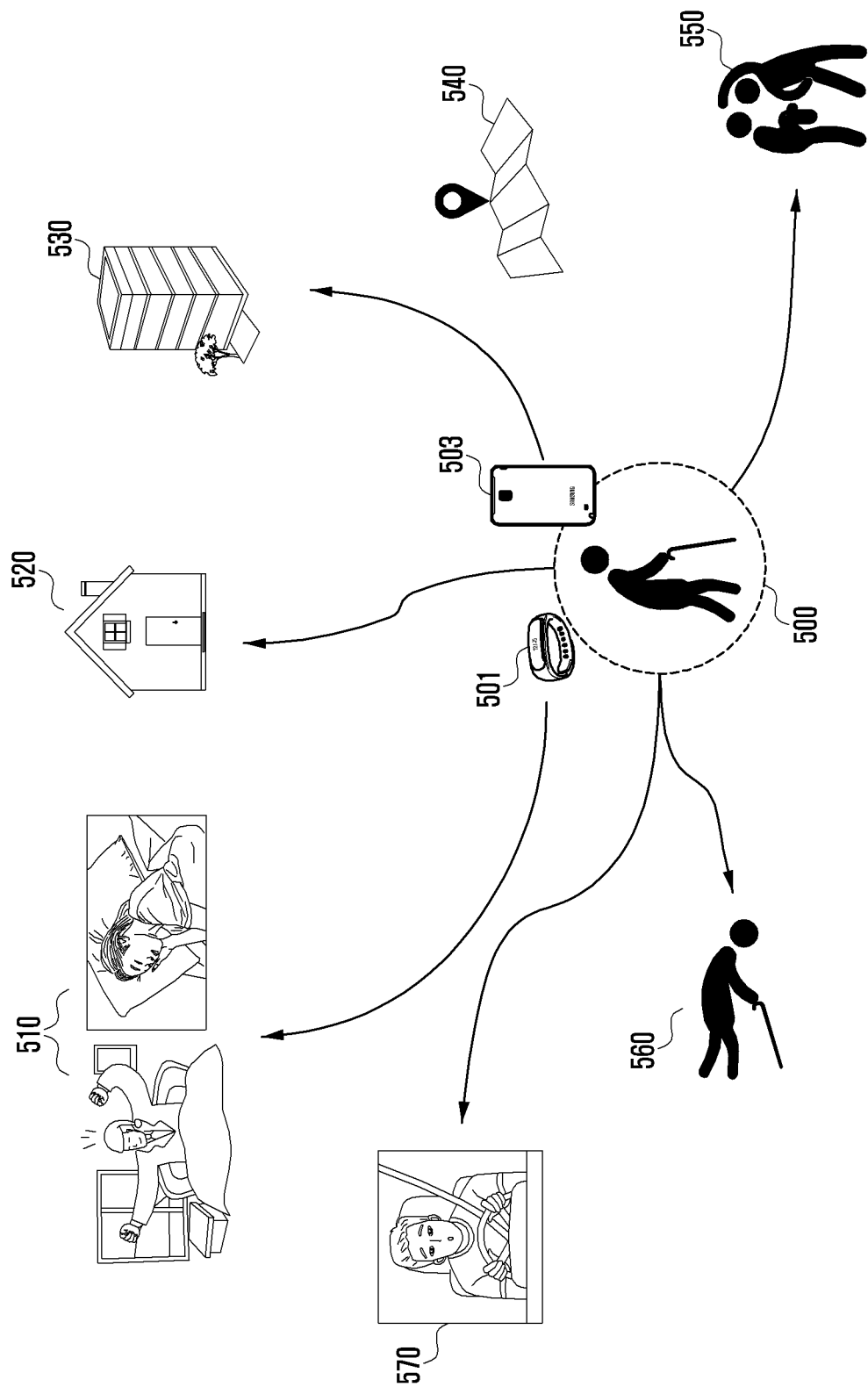
FIG. 5 is a diagram explaining a method for collecting sensor information according to various embodiments of the disclosure.

FIG. 5 is a diagram explaining a method for collecting sensor information according to various embodiments of the disclosure.

With reference to FIG. 5, a user 500 may wear an electronic device (e.g., electronic device 400 of FIG. 4), for example, a wearable device 501 and/or may carry a smart phone 503.

The electronic device (e.g., wearable device 501 and/or smart phone 503) may collect a sensor signal for motion of the electronic device and situation information including location information of the electronic device and time information on a time when the location information is collected.

The electronic device (e.g., wearable device 501 and/or smart phone 503) may monitor a user's getting-up/sleeping state 510, a user's home in/out state 520, a user's office in/out state 530, a location 540 that a user frequently visits, and a sensor-based user activity level 550 through analysis of the sensor signal for the motion of the electronic device. Further, the electronic device (e.g., wearable device 501 and/or smart phone 503) may detect a fall or non-motion state 560 through analysis of the sensor signal for the motion of the electronic device. For example, the electronic device may detect a fall accident through monitoring of the user activities. Further, the electronic device may detect the non-motion state through monitoring of a user's heartbeat. Further, the electronic device may detect whether a user is driving (570) through analysis of the sensor signal for the motion of the electronic device.

According to various embodiments of the disclosure, the electronic device may determine the pattern by analyzing the user's behavior and the situation information determined based on the sensor signal for the motion of the electronic device.

The electronic device may determine whether the determined pattern is different from the pattern pre-stored in the memory through comparison of the determined pattern with the pre-stored pattern. For example, the electronic device may determine whether the patterns are different from each other in accordance with the location of the electronic device, the time when the location is acquired, the user's behavior determined at the time, and the motion of the electronic device pre-stored in the memory (e.g., memory 420 of FIG. 4).

If the user's pattern is different from the pattern pre-stored in the memory as the result of the comparison, the electronic device may generate notification information based on information on the user's pattern, and it may transmit the generated notification information to an external electronic device.

Figure 6:
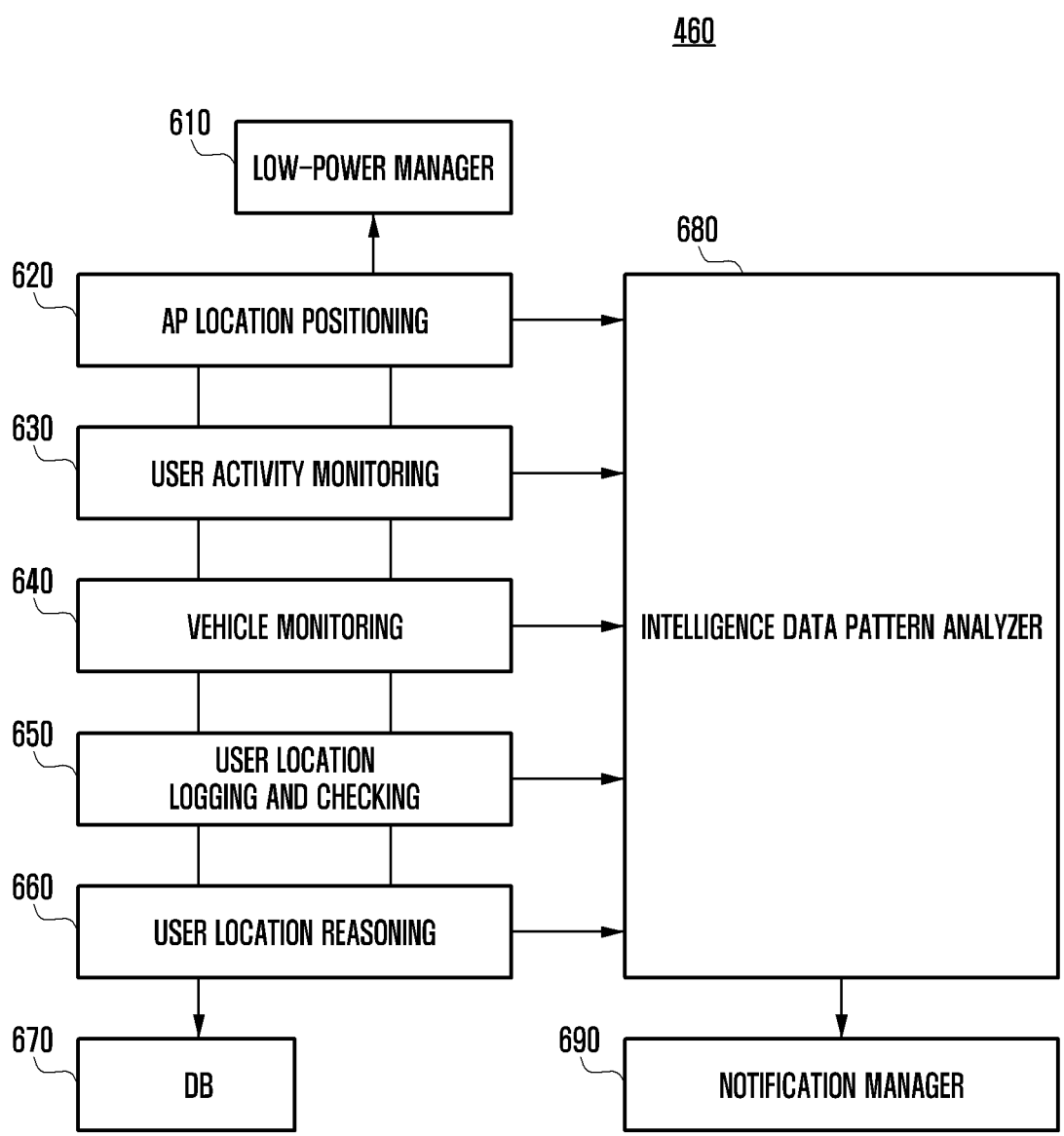
FIG. 6 is a block diagram explaining a method for providing a notification according to various embodiments of the disclosure.

FIG. 6 is a block diagram explaining a method for providing a notification according to various embodiments of the disclosure According to various embodiment of the disclosure, a processor 460 may include a low power manager 610, an access point (AP) location positioning 620, a user activity monitoring 630, a vehicle monitoring 640, a user location logging and checking 650, a user location reasoning 660, an intelligence data pattern analyzer 680, and a notification manager 690.

According to various embodiments of the disclosure, the low power manager 610 may perform positioning and collect locations of the electronic device (e.g., electronic device 400 of FIG. 4) with low power consumption in a predetermined condition.

According to various embodiments of the disclosure, the AP location positioning 620 may recognize whether the electronic device is located at a strongpoint using sensor information and situation information in accordance with the motion of the electronic device. According to various embodiments of the disclosure, the AP location positioning 620 may recognize a detailed location in the recognized strongpoint. The electronic device may provide a service in accordance with the detailed location in the strongpoint recognized by the AP location positioning 620.

According to various embodiments of the disclosure, if a user is located at the strongpoint, performable functions may be predetermined. For example, if it is recognized that the strongpoint at which a user is located is "home", the electronic device may control to perform a function of PC power-on.

According to various embodiments of the disclosure, a method for location positioning to through the AP location positioning 620 may include a wi-fi fingerprint technique. For example, a plurality of AP devices (e.g., wi-fi devices) may be installed in a place where the electronic device is located. The electronic device may receive AP information from the respective AP devices by performing scanning (e.g., wi-fi scan) of the AP devices for a predetermined time (e.g., 3 hours). The received AP information may include a service set identifier (SSID) that is an eigenvalue of a specific AP device received by the electronic device at a certain point (or location), a received signal strength indicator (RSSI), and a timestamp that means a character string indicating a time when a signal is received from the AP device. The electronic device may store the AP information that is received for the predetermined time at the certain point in a database (DB) 670 (e.g., memory 420 of FIG. 4).

According to various embodiments of the disclosure, the AP location positioning 620 may recognize the strongpoint based on the received AP information through scanning of the AP devices for the predetermined time. For example, the strongpoint may include home, office, detailed location in the home or office, and a frequently visited location.

According to various embodiments of the disclosure, the AP location positioning 620 may transfer, to the intelligence data pattern analyzer 680, whether a user is located at the strongpoint and information on the detailed location in the strongpoint if the user is located at the strongpoint.

According to various embodiments of the disclosure, the user activity monitoring 630 may determine the behavior of the user who uses the electronic device based on the sensor signal received by the sensor circuitry (e.g., sensor circuitry 440 of FIG. 4).

According to various embodiments of the disclosure, the behavior may include user's motion information (e.g., walking, running, and stop) and user's movement information using movement means (vehicle, bicycle, subway, elevator, escalator, and stairs).

According to various embodiments of the disclosure, sensor signals detected by the sensor circuitry (e.g., motion sensor, gyro sensor, magnetic sensor, and/or acceleration sensor) may differ by user's behaviors. For example, the sensor signal may include a frequency, a period, and an amplitude of the sensor signal.

For example, according to various embodiments of the disclosure, the user activity monitoring 630 may receive and collect sensor signals for user's behaviors detected for a predetermined time (e.g., 5 minutes) from a time when a user's specific behavior is detected. The user activity monitoring 630 may classify the user's behaviors in accordance with the similarity of the sensor signals collected in the process of collecting the sensor signals for the behaviors. For example, the user activity monitoring 630 may receive sensor signal a if user's behavior A is detected, receive sensor signal b if user's behavior B is detected, and receive sensor signal c if user's behavior C is detected. The user activity monitoring 630 may map and store, in a DB 670, the user's behaviors A, B, and C and the sensor signals a, b, and c corresponding to the respective behaviors.

The user activity monitoring 630 may determine the user's behavior through comparison of the sensor signal detected by, for example, the motion sensor, gyro sensor, magnetic sensor, and/or acceleration sensor with the sensor signal stored in the DB 670.

According to various embodiments of the disclosure, the user activity monitoring 630 may transfer information on the user's behavior to the intelligence data pattern analyzer 680.

According to various embodiments of the disclosure, the vehicle monitoring 640 may recognize whether a user takes or gets off a vehicle and whether to drive a vehicle.

According to various embodiments of the disclosure, the vehicle monitoring 640 may recognize whether to take or get off a vehicle and whether to drive the vehicle based on Bluetooth connection between the electronic device and the vehicle and vibration detected by the electronic device.

For example, the vehicle monitoring 640 may detect a Bluetooth connection between the electronic device and the vehicle. The vehicle monitoring 640 may recognize whether the user has taken or has got off the vehicle based on the sensed Bluetooth connection. According to various embodiments of the disclosure, if it is recognized that the user has taken the vehicle through the Bluetooth connection between the electronic device and the vehicle, the vehicle monitoring 640 may recognize whether the vehicle is being driven through analysis of the vibration of the electronic device. For example, if the vehicle is being driven, the vehicle monitoring 640 may recognize the vibration of the electronic device in accordance with the driving. For example, the electronic device may be mounted on a cradle of the vehicle, and the vehicle monitoring 640 may analyze the detected vibration in a state where the electronic device is mounted on the cradle. The vehicle monitoring 640 may determine whether the vehicle is being driven through comparison of the analyzed vibration pattern with the vibration pattern pre-stored in the DB 670.

According to various embodiments of the disclosure, the vehicle monitoring 640 may transfer information on whether the user has taken or has got off the vehicle and whether the vehicle is being driven to the intelligence data pattern analyzer 680.

According to various embodiments of the disclosure, the user location logging and checking 650 may recognize user's main strongpoints, for example, home, office, and frequently visited location through analysis of the location information of the electronic device and the time information on the time when the location information is acquired.

According to various embodiments of the disclosure, the user location logging and checking 650 may determine a range preconfigured based on the main strongpoint as user's main life radius, and it may check whether the user has seceded from the main life radius at a specific time.

According to various embodiments of the disclosure, the user location logging and checking 650 may transfer information on the recognized user's main strongpoint and whether the user has seceded from the main life radius based on the main strongpoint to the intelligence data pattern analyzer 680.

According to various embodiments of the disclosure, the user location reasoning 660 may perform map matching of the detailed information on a place in which the electronic device is periodically located. For example, the user location reasoning 660 may analogize and record the place through matching the location of the electronic device collected for a predetermined time with map data.

According to various embodiments of the disclosure, the user location reasoning 660 may transfer the location information recorded through the map matching to the intelligence data pattern analyzer 680.

According to various embodiments of the disclosure, the intelligence data pattern analyzer 680 may analyze the user's pattern based on the information received from the AP location positioning 620, the user activity monitoring 630, the vehicle monitoring 640, the user location logging and checking 650, and the user location reasoning 660.

For example, according to various embodiments of the disclosure, patterns in accordance with the motion of the electronic device, for example, a place in which the electronic device is located in accordance with the time, place movement order, time for which the electronic device stays in one place, average movement start time in the case of moving to another place, average movement end time, average movement consumption time, and movement means used during the movement, may be pre-stored in the DB 670.

The intelligence data pattern analyzer 680 may compare the analyzed user's pattern with the pattern pre-stored in the DB 670. If it is determined that the analyzed user's pattern is different from the pattern pre-stored in the DB 670 as the result of the comparison, the intelligence data pattern analyzer 680 may generate notification information based on the analyzed user's pattern. The intelligence data pattern analyzer 680 may transfer the generated notification information to the notification manager 690.

According to various embodiments of the disclosure, the notification manager 690 may transmit the notification information received from the intelligence data pattern analyzer 680 to at least one predesignated external electronic device.

Figure 7:
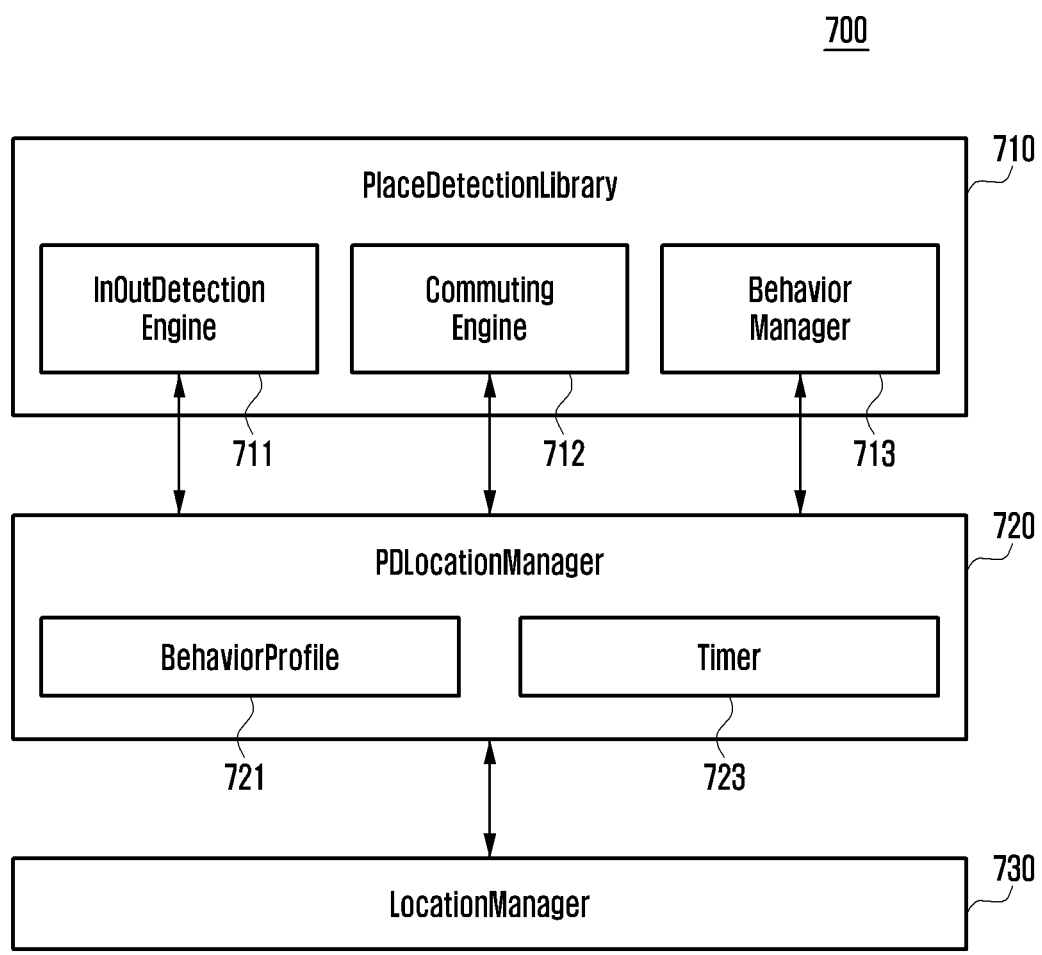
FIG. 7 is a block diagram illustrating a low-power location collection circuitry according to various embodiments of the disclosure.

FIG. 7 is a block diagram illustrating a low-power location collection circuitry according to various embodiments of the disclosure.

With reference to FIG. 7, a low-power location collection circuitry 700 (e.g., location collection circuitry 450 of FIG. 4) may include a place detection library 710, a PDlocation manager 720, and a location manager 730.

According to various embodiments of the disclosure, the place detection library 710 may include an in/out detection engine 711, a commuting engine 712, and a behavior manager 713.

According to various embodiments of the disclosure, the in/out detection engine 711 may detect a sensor signal for a strongpoint at which a user is located, for example, home in/out operation.

According to various embodiments of the disclosure, the commuting engine 712 may detect a sensor signal for a strongpoint at which a user is located, for example, office in/out operation.

According to various embodiments of the disclosure, the behavior manager 713 may recognize the user's behavior based on the sensor signal detected through the sensor circuitry (e.g., sensor circuitry 440 of FIG. 4).

According to various embodiments of the disclosure, the place detection library 710 may transfer a signal for a request for location collection of the electronic device to the PDlocation manager 720. The place detection library 710 may receive the location information from the PDlocation manager 720 to process the received location information. The place detection library 710 may transfer, to the PDlocation manager 720, the user's pattern (e.g., user's motion information, a place in which the electronic device is located in accordance with time, a time when the electronic device stays in one place, and user's movement information using movement means) recognized by the in/out detection engine 711, the commuting engine 712, and the behavior manager 713.

According to various embodiments of the disclosure, the PDlocation manager 720 may include a behavior profile 721 and a timer 723.

According to various embodiments of the disclosure, the behavior profile 721 may store a user's behavior. For example, according to various embodiments of the disclosure, the behavior may include user's motion information (e.g., walking, running, and stop) and user's movement information using movement means (vehicle, bicycle, subway, elevator, escalator, and stairs).

According to various embodiments of the disclosure, the timer 723 may measure the time for which the user's behavior received from the place detection library 710 is maintained.

The PDlocation manager 720 may manage the behavior received from the place detection library 710, the time for which the behavior measured by the timer 723 is maintained, and the situation information, and it may determine the time when the location is collected based on this.

According to various embodiments of the disclosure, the location manager 730 may collect the location of the electronic device using at least one of a network location provider (NLP), GPS, cell location, and passive provider at the time determined by the PDlocation manager 720.

According to various embodiments of the disclosure, the low-power location collection circuitry 700 may collect the location information with low power consumption through activation of at least one of a strongpoint recognition low-power mode, a low-power activity data collection mode, and a low-power location data collection mode in a predetermined condition. This will be described in detail with reference to FIGS. 8 to 14.

Figure 8:
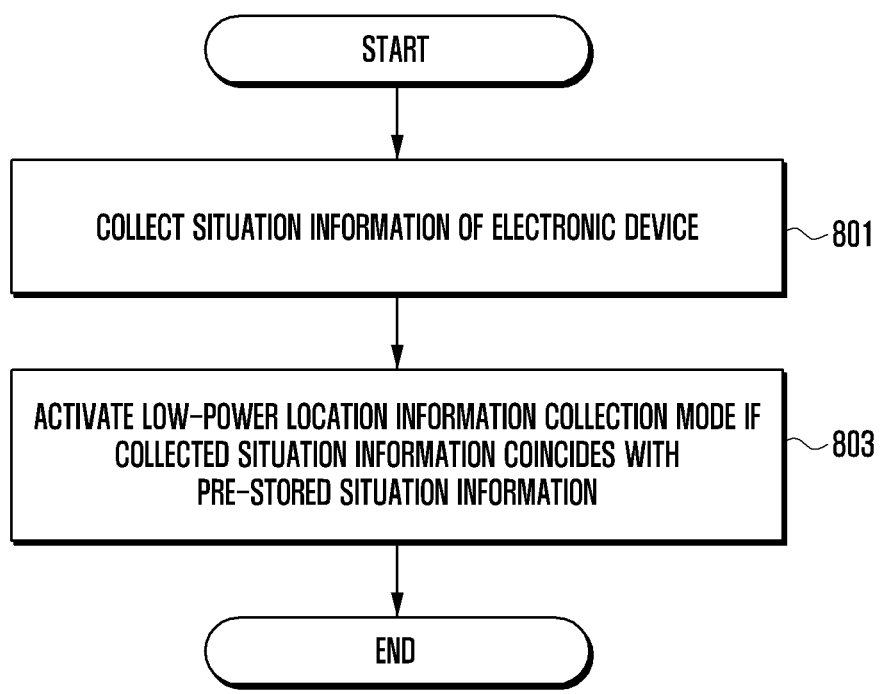
FIG. 8 is a flowchart explaining a method for collecting location information with low power consumption according to various embodiments of the disclosure.

FIG. 8 is a flowchart explaining a method for collecting location information with low power consumption according to various embodiments of the disclosure.

With reference to FIG. 8, at operation 801, an electronic device (e.g., electronic device 400 of FIG. 4) may collect situation information of the electronic device.

According to various embodiments of the disclosure, the electronic device may collect the situation information including location information in accordance with the motion of the electronic device and time information about the time when the location information is acquired. The location information may be collected at a predetermined time interval.

If the collected situation information coincides with the situation information pre-stored in the memory (e.g., memory 420 of FIG. 4), the electronic device, at operation 803, may activate a mode for collecting the location information with low power consumption.

This will be described in detail with reference to FIG. 9.

Figure 9:
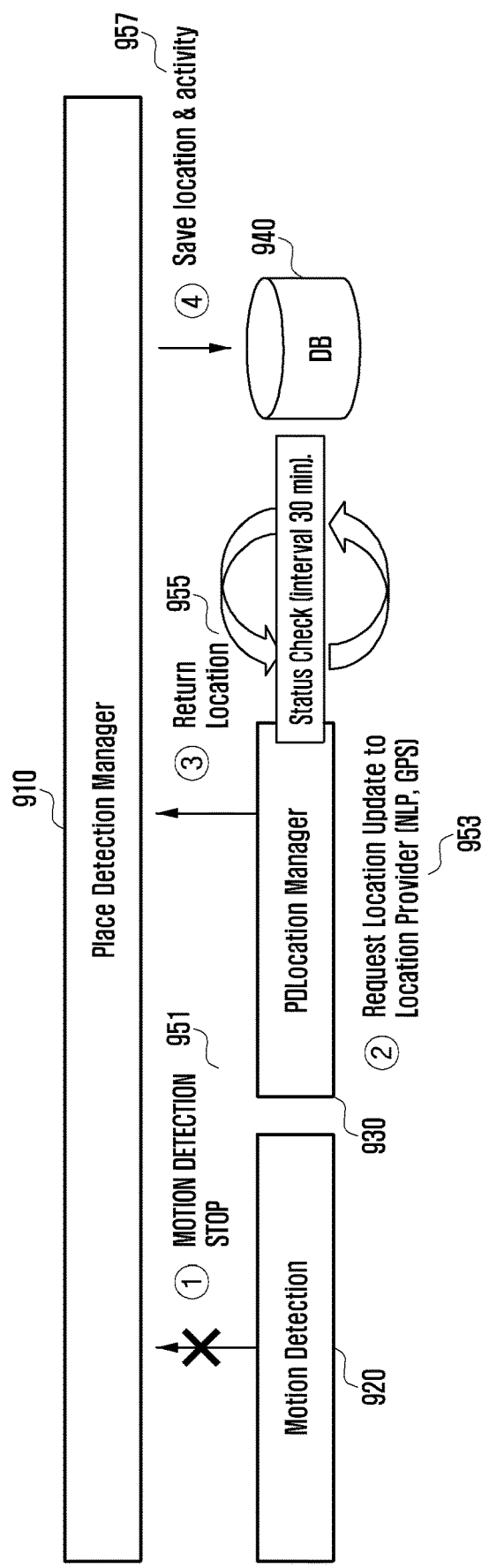
FIG. 9 is a block diagram explaining a strongpoint recognition low-power mode according to various embodiments of the disclosure.

FIG. 9 is a block diagram explaining a strongpoint recognition low-power mode according to various embodiments of the disclosure.

With reference to FIG. 9, according to various embodiments of the disclosure, a place detection manager 910 may activate a low-power location collection mode at a specific strongpoint. According to various embodiments of the disclosure, the strongpoint may include at least one of home, office, and frequently visited location. Among the strongpoints, the specific strongpoint may be configured by a user as a place in which the low-power location collection mode is to be activated, but it is not limited thereto.

According to various embodiments of the disclosure, if the user is located at the specific strongpoint and thus the low-power location collection mode is activated, the electronic device may stop a motion detection 920 and an activity detection (not illustrated) (951).

According to various embodiments of the disclosure, the PDlocation manager 930 may identify the state of the electronic device at a predetermined time interval (e.g., 30 minutes). For example, the electronic device may request the location collection circuitry, for example, a location provider (e.g., NLP or GPS), to provide the current location of the electronic device at the predetermined time interval (953).

According to various embodiments of the disclosure, if the location collected at the predetermined time interval is still at the strongpoint, the electronic device may maintain the stop state of the motion detection 920 and the activity detection. In contrast, if the location collected at the predetermined time interval is not still at the strongpoint, the electronic device may activate the motion detection 920 and the activity detection.

According to various embodiments of the disclosure, the PDlocation manager 930 may transfer the current location of the electronic device collected in accordance with the request to the place detection manager 910 (955). The place detection manager 910 may store the location information and the activity received from the PDlocation manager 930 in the database (DB) 940.

According to various embodiments of the disclosure, if it is recognized that the current location of the electronic device is "home" on the assumption that the strongpoint for activating the low-power location collection mode is "home", the electronic device may activate the low-power location collection mode during a time schedule for the electronic device to be located at "home" (e.g., from 7:00 pm to 8:00 am).

According to various embodiments of the disclosure, the time schedule may be periodically updated through pattern analysis in accordance with the motion of the electronic device.

Figure 10:
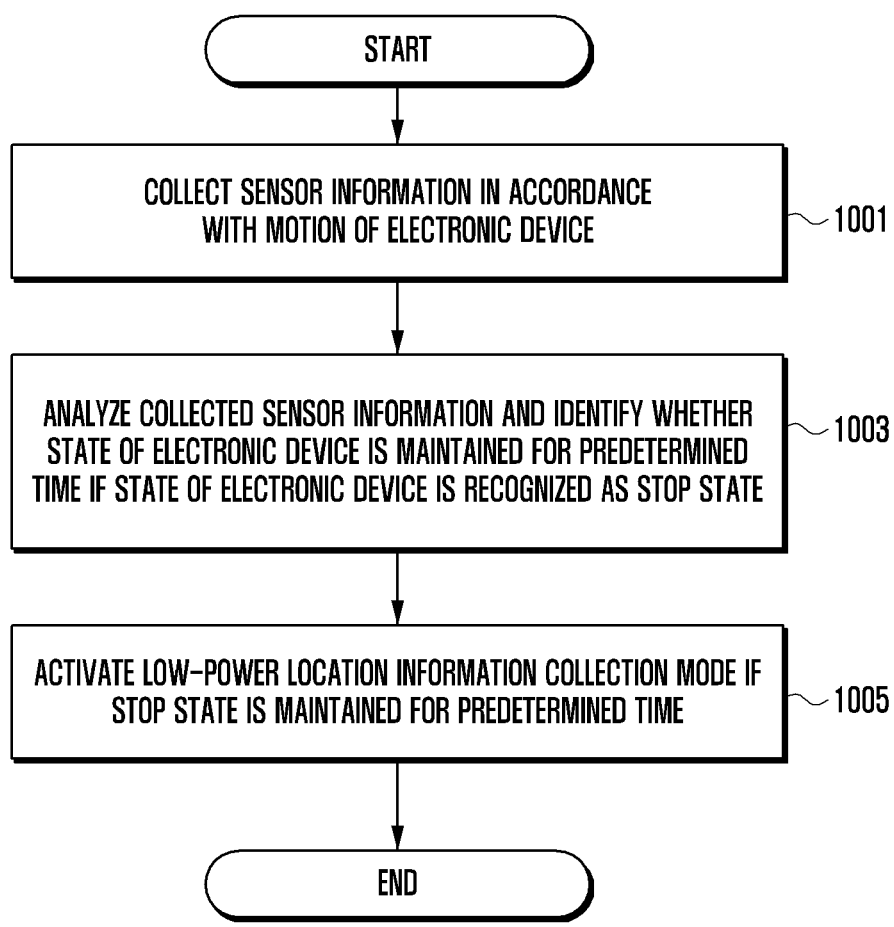
FIG. 10 is a flowchart explaining a method for collecting location information with low power consumption according to various embodiments of the disclosure.

FIG. 10 is a flowchart explaining a method for collecting location information with low power consumption according to various embodiments of the disclosure.

With reference to FIG. 10, at operation 1001, an electronic device (e.g., electronic device 400 of FIG. 4) may collect sensor information in accordance with a motion of the electronic device.

According to various embodiments of the disclosure, the electronic device may receive sensor signals using a sensor circuitry (e.g., sensor circuitry 400 of FIG. 4), for example, a motion sensor, an acceleration sensor, a magnetic sensor, and/or a gyro sensor.

If it is recognized that the electronic device is in a stop state based on the collected sensor information, the electronic device, at operation 1003, may determine whether the stop state is maintained for a predetermined time. For example, if the sensor signal is not received from the sensor circuitry, the electronic device may determine that a user who uses the electronic device does not move, and it may recognize that the electronic device is in the stop state.

If the recognized stop state is maintained for a predetermined time, the electronic device, at operation 1005, may activate a low-power location information collection mode.

According to various embodiments of the disclosure, if user's behavior is changed, for example, if the motion of the electronic device is detected, in a state where the low-power location information collection mode is activated, the electronic device may inactivate the activated low-power location information collection mode, branch to operation 1001, and collect the sensor information in accordance with the motion of the electronic device.

This will be described in detail with reference to FIG. 11.

Figure 11:
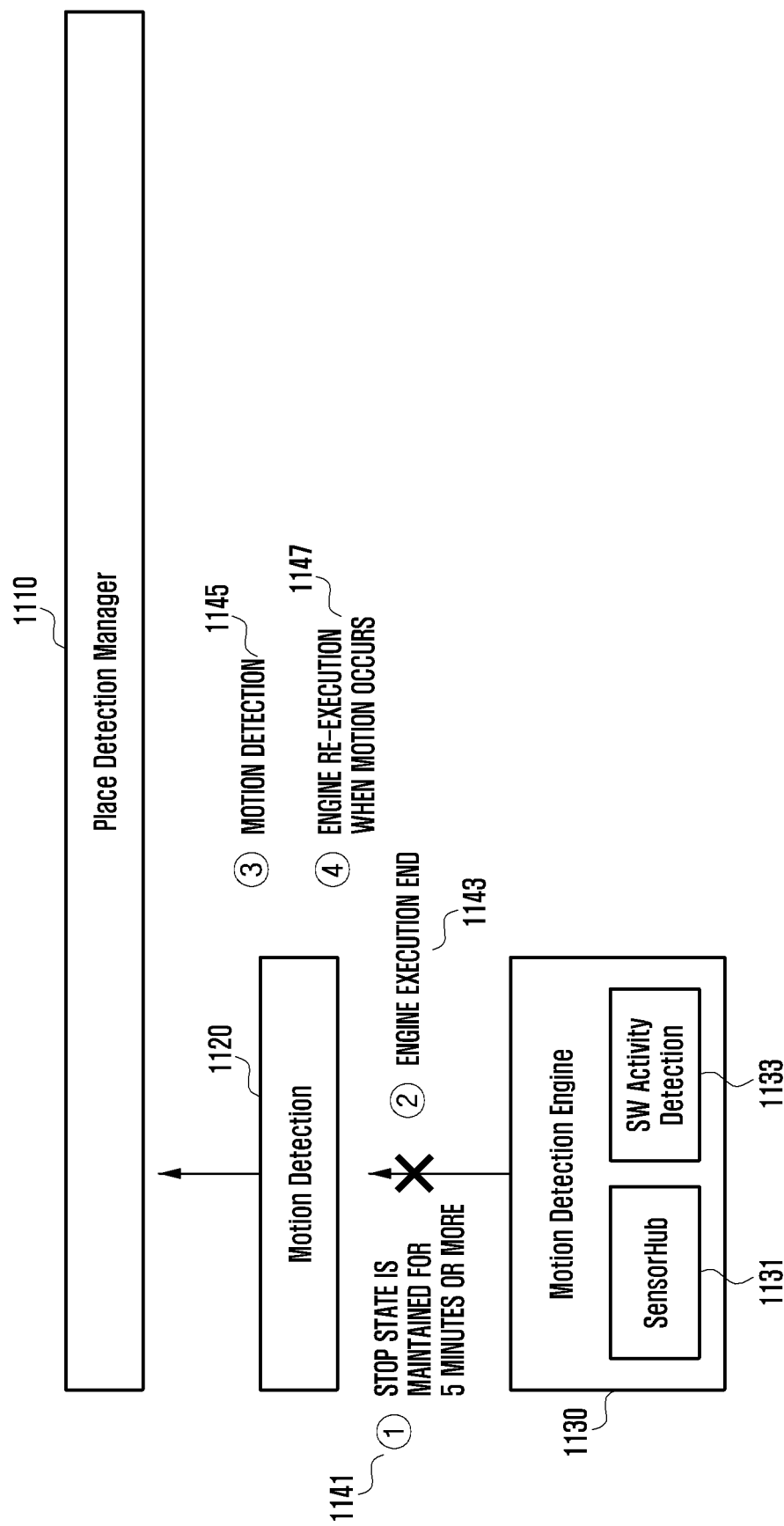
FIG. 11 is a block diagram explaining a low-power activity data collection mode according to various embodiments of the disclosure.

FIG. 11 is a block diagram explaining a low-power activity data collection mode according to various embodiments of the disclosure.

With reference to FIG. 11, according to various embodiments of the disclosure, software may be used as activity detection. Motion detection 1120 may detect a motion of an electronic device (electronic device 400 of FIG. 4).

The motion detection 1120 may transfer information on the motion of the electronic device to a place detection manager 1110.

According to various embodiments of the disclosure, if the motion of the electronic device is not detected by the motion detection 1120, the electronic device may determine that the electronic device is in a stop state.

The electronic device may determine whether the stop state is maintained for a predetermined time (e.g., 5 minutes). If the stop state is maintained for the predetermined time, the electronic device may activate a low-power activity data collection mode. For example, if the stop state is maintained for the predetermined time, the electronic device may end an execution of a motion detection engine 1130 including a sensor hub 1131 and a software (SW) activity detection 1133 (1143).

According to various embodiments of the disclosure, after entering into the low-power activity data collection mode in accordance with an end of the execution of the motion detection engine 1130, the electronic device may determine whether the motion of the electronic device is detected at a predetermined time interval (e.g., 10 minutes) using only a specific sensor, for example, only an acceleration sensor (1145).

If the motion of the electronic device is detected, the electronic device may re-execute the ended motion detection engine 1130 (1147).

Figure 12:
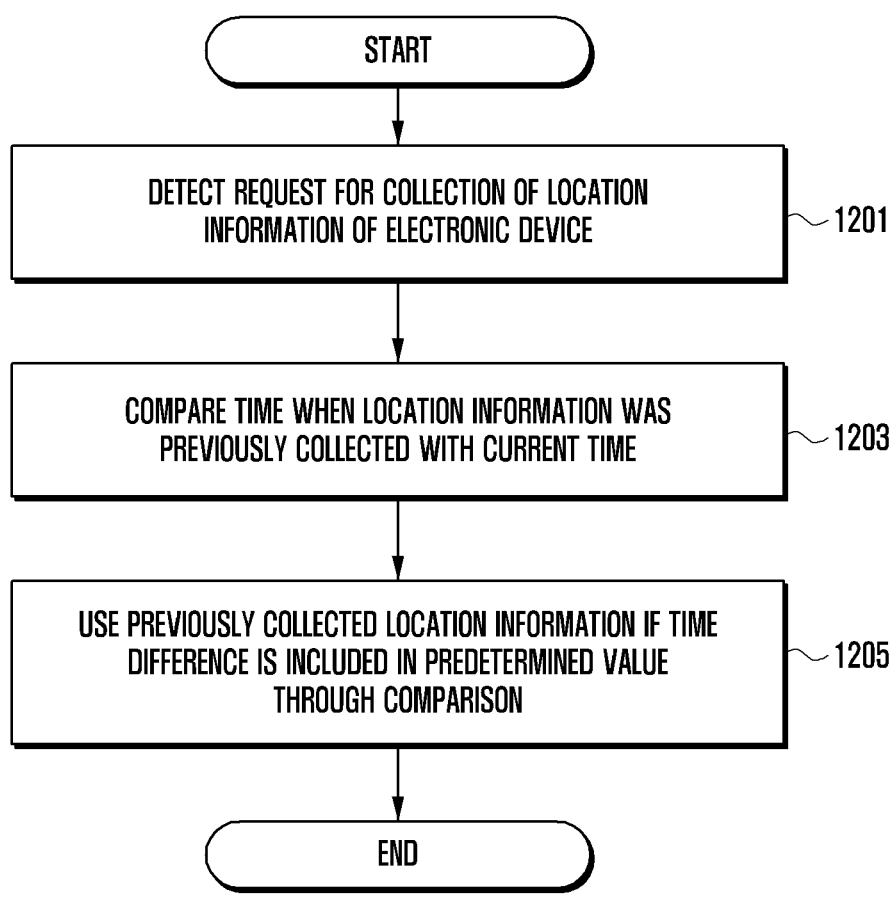
FIG. 12 is a flowchart illustrating a method for collecting location information with low power consumption according to various embodiments of the disclosure.

FIG. 12 is a flowchart illustrating a method for collecting location information with low power consumption according to various embodiments of the disclosure.

With reference to FIG. 12, at operation 1201, an electronic device (e.g., electronic device 400 of FIG. 4) may detect a request for collection of location information of the electronic device.

In response to the request for collection of location information, the electronic device, at operation 1203, may compare the time when the location information was previously collected with the current time.

If a time difference obtained through the comparison is included in a predetermined value (e.g., if the time difference is within 10 minutes), the electronic device, at operation 1205, may use the previously collected location information.

According to various embodiments of the disclosure, if the difference between the time when the location information was previously collected and the current time is included in the predetermined value, the electronic device may use the previously collected location information instead of acquiring the location information through the location collection circuitry, and thus power consumption can be reduced.

Figure 13:
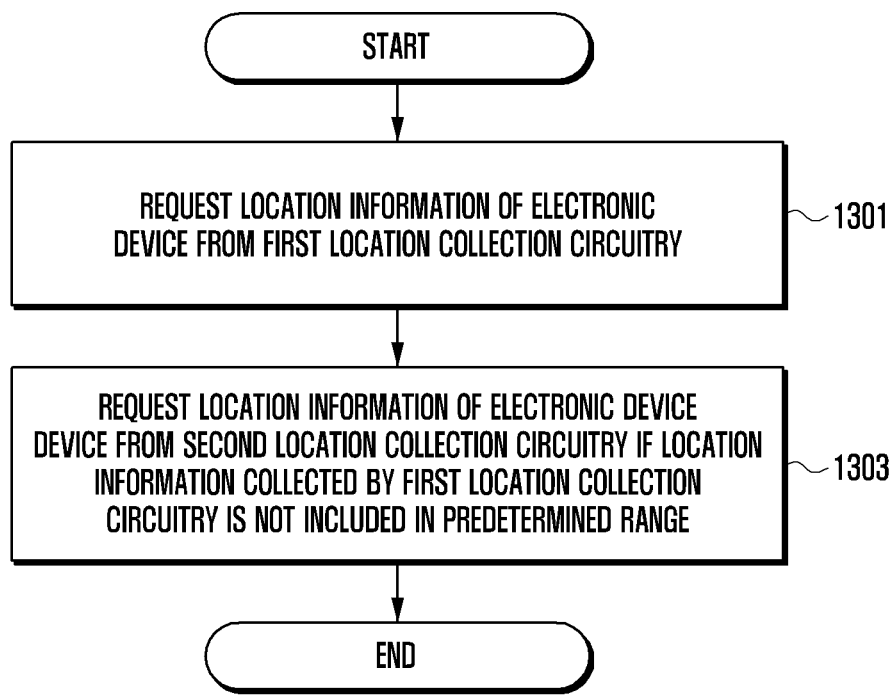
FIG. 13 is a flowchart illustrating a method for collecting location information with low power consumption according to various embodiments of the disclosure.

FIG. 13 is a flowchart illustrating a method for collecting location information with low power consumption according to various embodiments of the disclosure.

With reference to FIG. 13, at operation 1301, an electronic device (e.g., electronic device 400 of FIG. 4) may request a first location collection circuitry (e.g., network provider) to provide location information of the electronic device.

If the location information collected by the first location collection circuitry is not included in a predetermined range, the electronic device, at operation 1303, may request a second provider (e.g., GPS) to provide the location information of the electronic device 400.

The power consumption of the first location collection circuitry may be lower than the power consumption of the second location collection circuitry.

According to various embodiments of the disclosure, the location information is preferentially requested from the first location collection circuitry, and thus the power consumption can be reduced.

Figure 14:
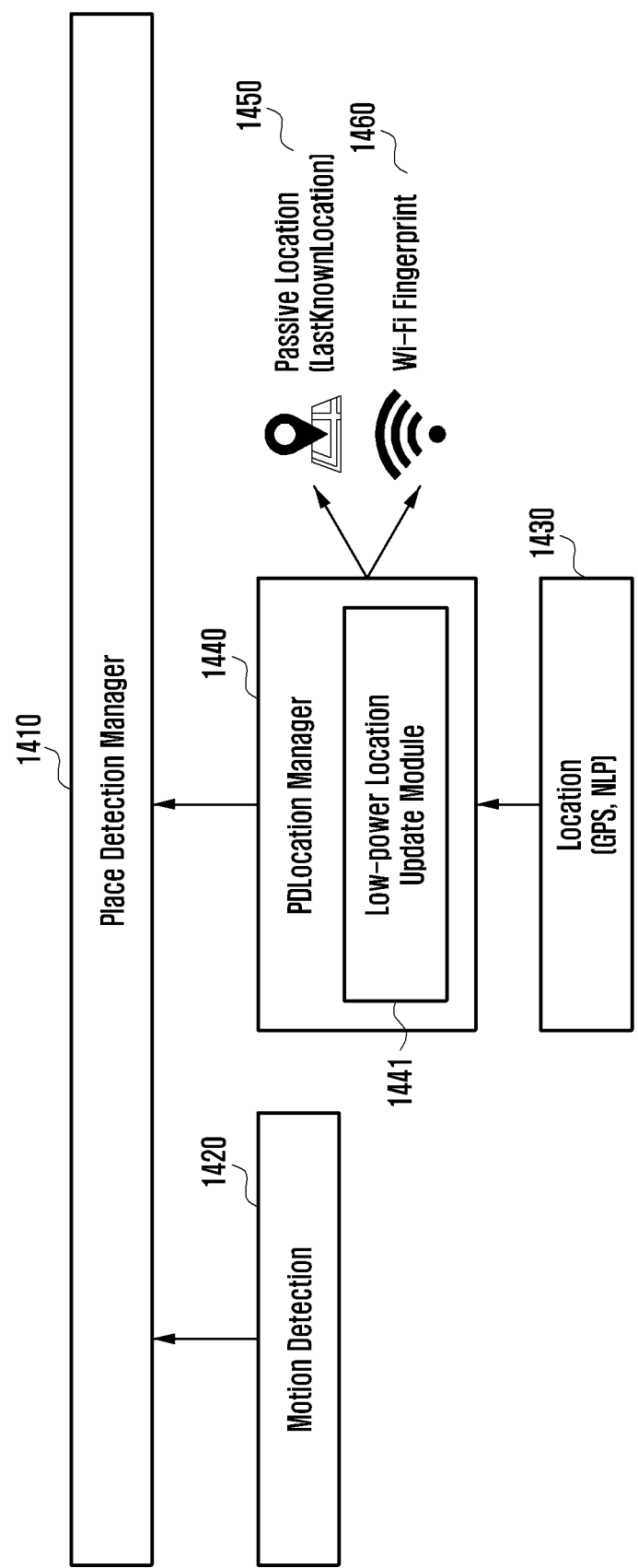
FIG. 14 is a block diagram explaining a low-power location data collection mode according to various embodiments of the disclosure.

FIG. 14 is a block diagram explaining a low-power location data collection mode according to various embodiments of the disclosure.

According to various embodiments of the disclosure, an electronic device (e.g., electronic device 400 of FIG. 4) may use location information collected by another service and application, or it may collect location information with low power consumption through wi-fi fingerprint.

With reference to FIG. 14, if a motion of an electronic device is detected, a motion detection 1420 may transfer information on this to a place detection manager 1410.

According to various embodiments of the disclosure, a location 1430 may collect location information using at least one of NLP and GPS. For example, the electronic device may preferentially request the NLP having low power consumption to provide the location information. If the accuracy of the location information collected by the NLP is within a reference range (e.g., if the strongpoint radius is 400 m or more), the electronic device may request the GPS to provide the location information.

According to various embodiments of the disclosure, the location 1430 may transfer the location information to a PDLocation manager 1440. The PDLocation manager 1440 may include a low-power location update module 1441. The low-power location update module 1441 may update the location information with low power consumption using at least one technique of a lastknownlocation 1450 and a wi-fi fingerprint 1460.

According to various embodiments of the disclosure, if a difference between the time for the lastknownlocation 1450 (or time information of the previously collected location) and the current time is included, for example, within 10 minutes, the electronic device may reuse the information on the lastknownlocation.

According to various embodiments of the disclosure, if the location information previously collected through the wi-fi fingerprint 1460 is equal to the currently collected location information, the electronic device may reuse the location information. After reusing the lastknownlocation and the location information collected through the wi-fi fingerprint, the electronic device may control not to request the location information for a predetermined time.

According to various embodiments of the disclosure, even if the collection of the location information is not possible, the electronic device may control not to request the collection of the location information for the predetermined time, and thus power consumption can be reduced.

According to various embodiments of the disclosure, the PDLocation manager 1440 may transfer the location information of the electronic device to the place detection manager 1410.

FIGS. 15A to 15D are diagrams illustrating a method for reasoning a user's location according to various embodiments of the disclosure.

Figure 15A:
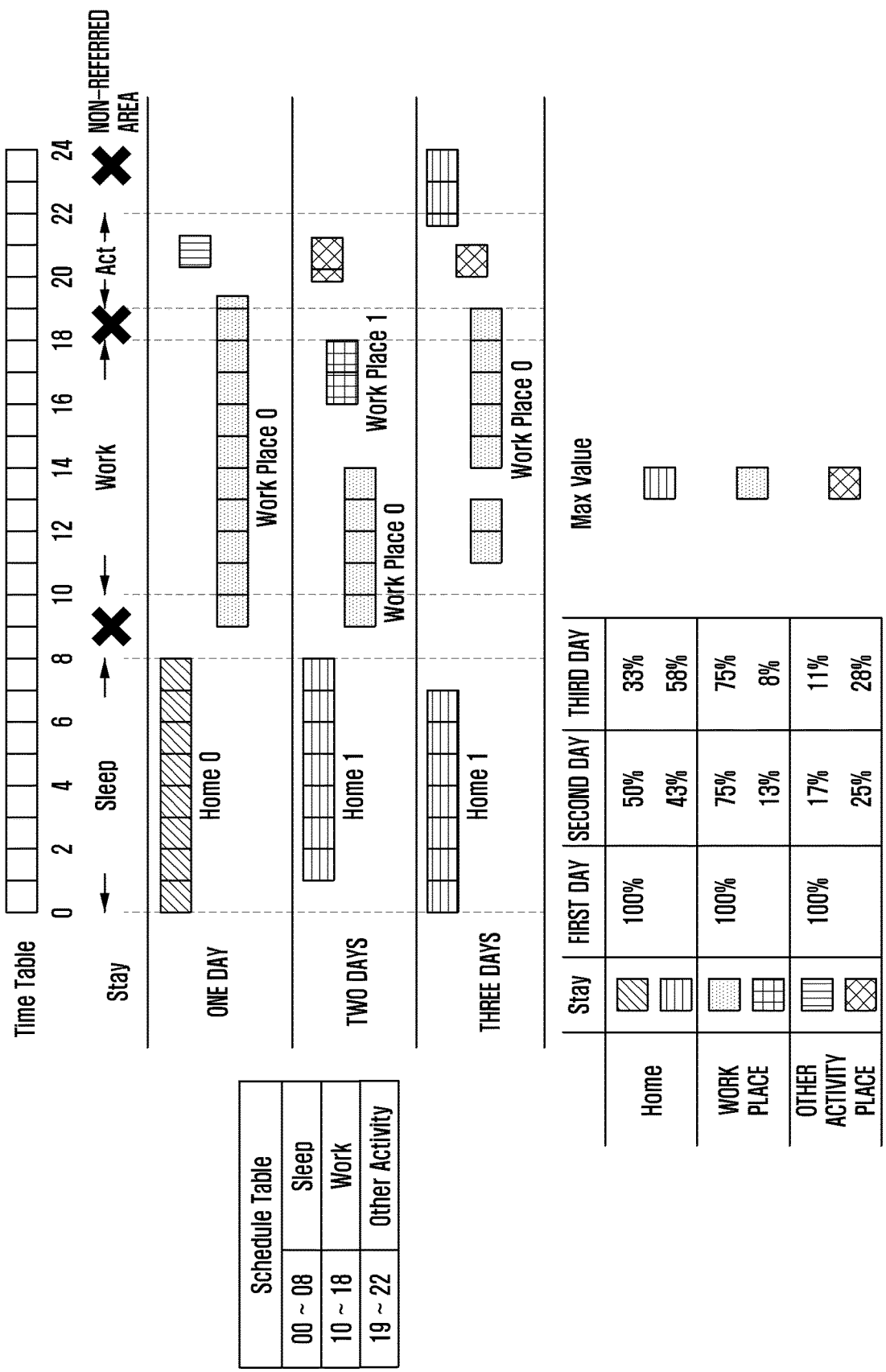
FIG. 15A is a diagram illustrating a method for reasoning a user's location according to various embodiments of the disclosure.
Figure 15B:
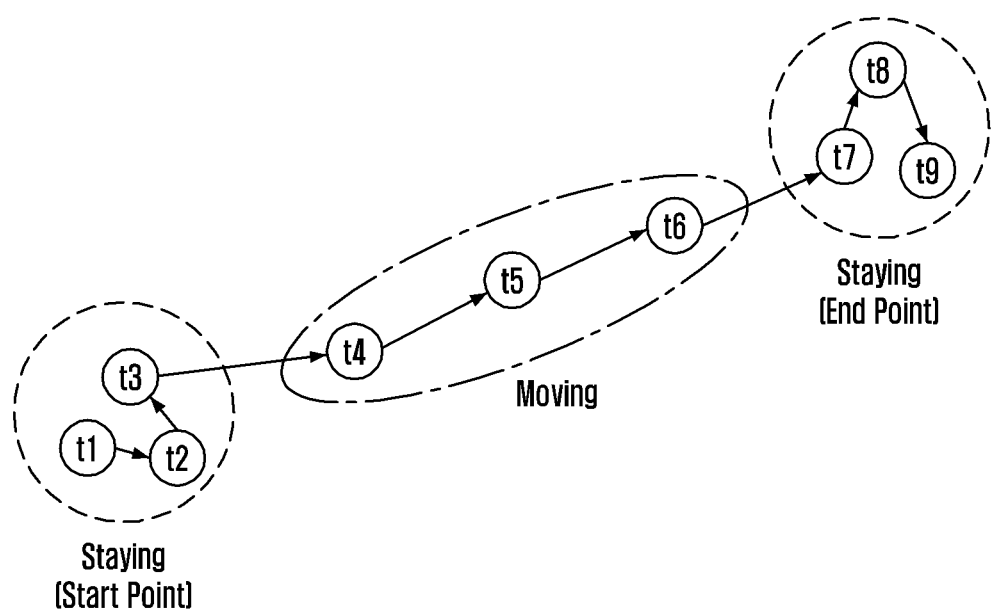
FIG. 15B is a diagram illustrating a method for reasoning a user's location according to various embodiments of the disclosure.
Figure 15C:
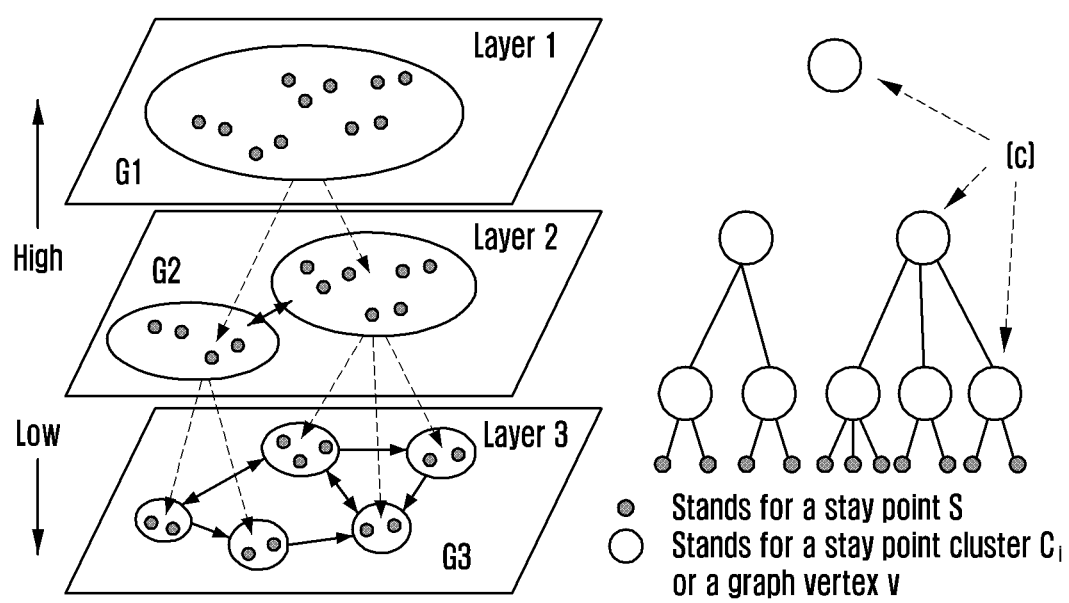
FIG. 15C is a diagram illustrating a method for reasoning a user's location according to various embodiments of the disclosure.
Figure 15D:
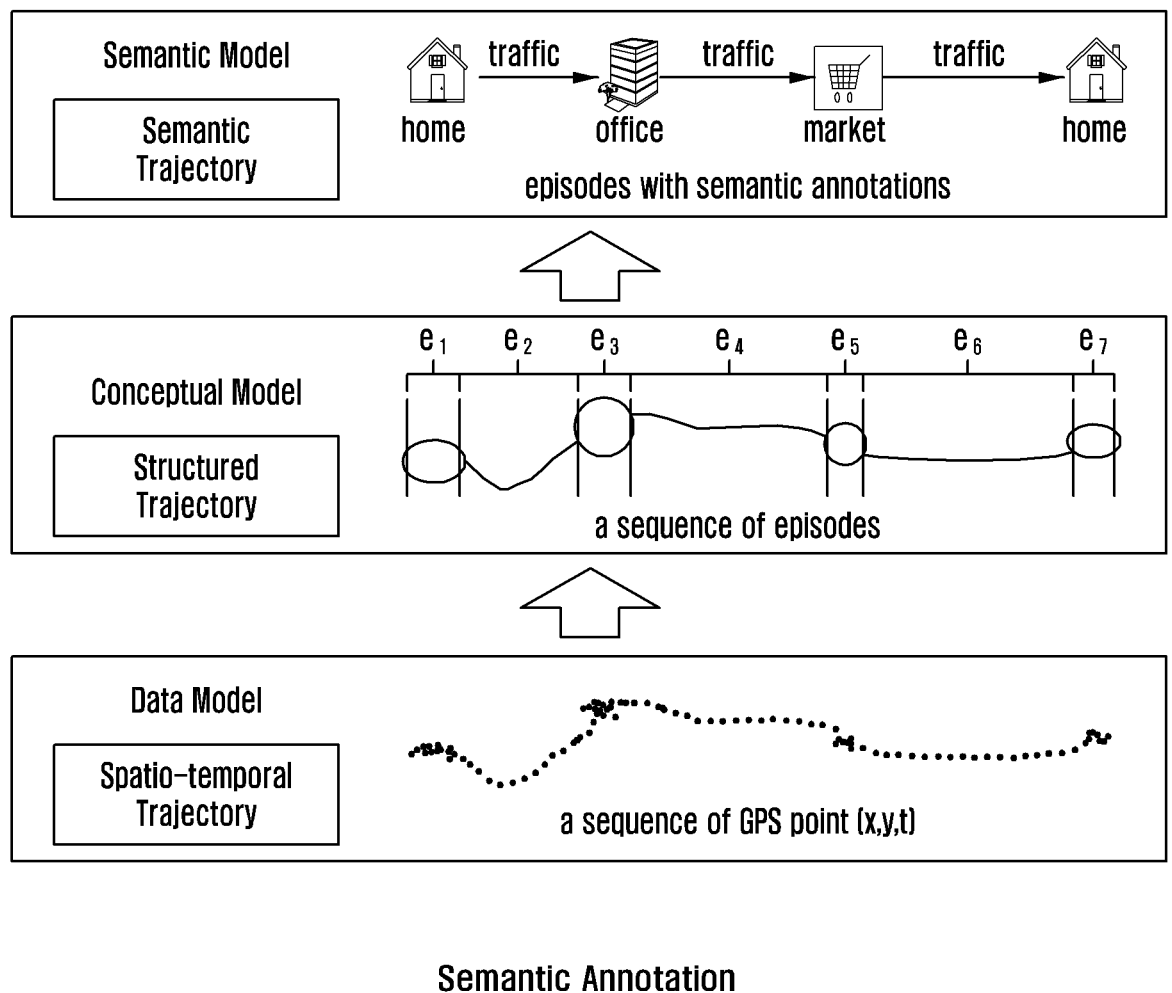
FIG. 15D is a diagram illustrating a method for reasoning a user's location according to various embodiments of the disclosure.

With reference to FIG. 15A, an electronic device (e.g., electronic device 400 of FIG. 4) may collect sensor information and situation information on the electronic device for a predetermined time. The electronic device may analyze a pattern based on the collected sensor information and situation information. For example, based on the collected sensor information and situation information, the electronic device may analyze the pattern including at least one of a place (e.g., home or office) in which the electronic device is located in accordance with time, place movement order, time for which the electronic device stays in one place, average movement start time in the case of moving to another place, average movement end time, average movement consumption time, and movement means (e.g., vehicle, subway, and elevator) during the movement.

For example, based on mathematical expression 1 below, a place in which the electronic device is located in accordance with time may be analyzed.

[Mathematical expression 1]

$$P = P(T_{stay} \mid T_{schedule}) * \frac{\text{overlap time per place}}{\text{whole overlap time}}$$

overlap ratio of (home/work) stay time and (home/work) schedule

The user location reasoning (e.g., user location reasoning 660 of FIG. 6) may automatically search for home, office, and frequently visited location through analysis of the user's strongpoint based on the sensor information and the situation information.

According to various embodiments of the disclosure, as illustrated in FIGS. 15A to 15D, similarity in accordance with the situation information and the sensor information of the electronic device may be determined, and if the similarity is equal to or higher than a reference value, clustering may be performed in the same location. For example, t1 to t3 may be clustered in a standby state (start point), t4 to t6 are clustered in a motion state, and t7 to t9 are clustered in a standby state (end point). Through hierarchical location modeling based on the clustered location, a user's strongpoint (e.g., home, office, and frequently visited location) and a detailed location of the strongpoint can be automatically extracted, and the pattern can be defined through semantic annotation. For example, the electronic device may define user in/out pattern, office in/out pattern, main place visit time and in/out pattern, and place movement pattern.

Figure 16:
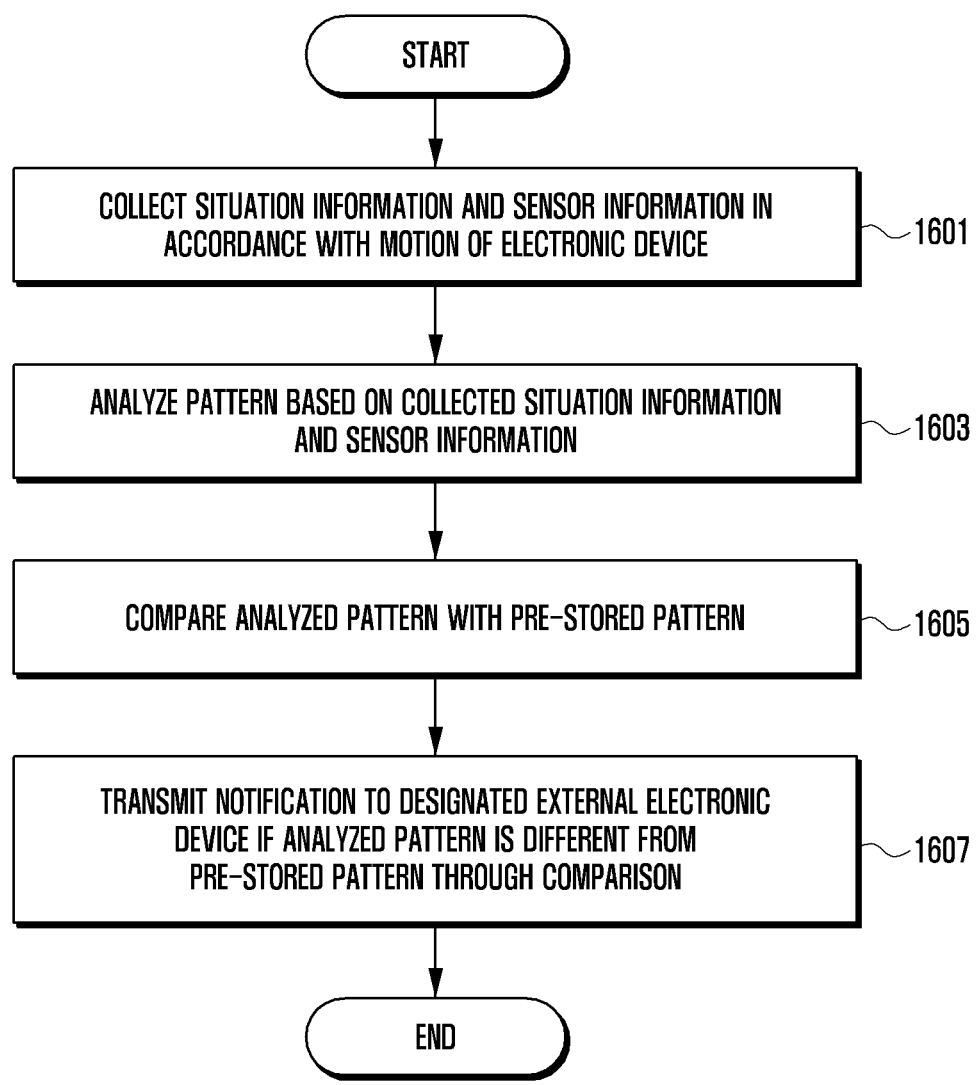
FIG. 16 is a flowchart illustrating a method for providing a notification according to various embodiments of the disclosure.

FIG. 16 is a flowchart illustrating a method for providing a notification according to various embodiments of the disclosure.

With reference to FIG. 16, at operation 1601, an electronic device (e.g., electronic device 400 of FIG. 4) may collect situation information and sensor information on a motion of the electronic device.

According to various embodiments of the disclosure, the situation information on the motion of the electronic device may include location information of the electronic device and time information on the time when the location information is acquired.

According to various embodiments, the electronic device may acquire the location information of the electronic device through a location collection circuitry (e.g., location collection circuitry 450 of FIG. 4). The electronic device may map the acquired location information to the time information on the time when the location information is acquired, and it may store the mapped information in a memory (e.g., memory 420 of FIG. 4).

According to various embodiments of the disclosure, the electronic device may determine a user's behavior based on sensor signals received by a sensor circuitry (e.g., sensor circuitry 440 of FIG. 4), for example, a motion sensor, an acceleration sensor, a magnetic sensor, and/or gyro sensor.

According to various embodiments of the disclosure, the user's behavior may include user's motion information (e.g., walking, running, and step) and user's movement information using movement means (vehicle, bicycle, subway, elevator, escalator, and stairs).

According to various embodiments of the disclosure, sensor signals received through the sensor circuitry by user's behaviors may differ from each other. The sensor signal for the behavior may be stored in the memory (e.g., memory 420 of FIG. 4) as a reference value. The electronic device may determine the user's behavior through comparison of the sensor signal received through the sensor circuitry with the sensor signal pre-stored in the memory.

At operation 1603, the electronic device may analyze a pattern of the electronic device based on the collected situation information and sensor information.

At operation 1605, the electronic device may compare the pattern analyzed at operation 1605 with the pre-stored pattern.

If the analyzed pattern is different from the pre-stored pattern through the comparison operation, the electronic device, at operation 1607, may transmit notification information to a predesignated external electronic device.

According to various embodiments of the disclosure, the notification information may be generated based on the sensor information and the situation information as described in Table 1 below.

According to various embodiments of the disclosure, if the analyzed pattern is different from the pre-stored pattern through the comparison operation, it has been described that the electronic device transmits the notification information generated based on the sensor information and the situation information to the pre-stored external electronic device, but transmission of the notification information is not limited thereto.

For example, the electronic device may transmit the analyzed pattern information to the designated external electronic device through the wireless communication circuitry (e.g., wireless communication circuitry 410 of FIG. 4).

According to various embodiments of the disclosure, the notification as described in Table 1 can be provided using the electronic device. Hereinafter, various utilization examples of the electronic device according to the disclosure will be described.

TABLE 1

| Notification information in the related art | Notification information of disclosure |
| --- | --- |
| Father went out of home at 10:00. | Father went out of home at 10:00 that is one hour later than ordinary times. |
| Notification is not provided if there is not a getting-up event. | Father did not get up. Please contact him in his house. |
| Father got up at 6:00. | Father got up at 6:00. His expected sleep time is 7 hours. It is an average sleep time. |
| Father is out | Father is staying in an area that deviates from his usual life radius. Current heart rate is normal, and he is currently walking. |
| Father returned home at 8:30. | Father returned home two hours later than ordinary times. Today's movement distance is 4 Km, and an average number of steps is 4300. |
| Fall was recognized. | Fall was recognized. The behavior recognized before the fall was going downstairs, and the current heart rate is descending. The fall location is area A. |

As described in Table 1, in the related art, only information on the user's motion is simply provided, whereas according to various embodiments of the disclosure, user's life pattern, traffic line, and activities can be monitored through the situation information of the electronic device and sensors provided in the electronic device, and notification information for combining them can be provided.

For example, according to various embodiments of the disclosure, it is assumed that a user is a father, a user of a pre-designated external electronic device is a son, and a pattern pre-stored in a memory is a pattern in which the father goes out of home at 9:00 for work.

According to various embodiments of the disclosure, if the pattern pre-stored in the memory is the pattern of going out of home at 9:00 for work, and the pattern collected by the electronic device is the pattern of going out of hem at 10:00 for work, the electronic device may generate notification information "Father went out of home at 10:00 that is one hour later than ordinary times", and it may transmit the notification information to the pre-stored external electronic device, for example, to the son. Accordingly, the son may grasp the father's situation through the received notification information.

According to various embodiments of the disclosure, information on the time when a specific behavior is detected may be transmitted to the external electronic device. For example, if the sensor signal detected by the electronic device is determined "fall", the electronic device may generate notification information "The behavior recognized before the fall was going downstairs, and the current heart rate is descending. The fall location is area A", and the electronic device may transmit this notification information to the user of the pre-stored external electronic device, for example, to the son. Accordingly, the son can promptly cope with an emergency situation through grasping of the father's situation in accordance with the received notification information.

Although the electronic device and the method for providing a notification using the same according to the preferred embodiments of the disclosure have been described in the specification and drawings and specific wordings have been used, these are merely used as general meanings to assist those of ordinary skill in the art to gain a comprehensive understanding of the disclosure, and do not limit the scope of the disclosure. It will be apparent to those of ordinary skill in the art to which the disclosure pertains that various embodiments are possible based on the technical concept of the disclosure.

The invention claimed is:

1. An electronic device comprising:
a wireless communication circuitry;
a sensor circuitry;
a location collection circuitry;
a memory; and
a processor electrically connected to the wireless communication circuitry, the sensor circuitry, the location collection circuitry, and the memory,
wherein the memory, when executed, includes instructions to
cause the processor to collect at least one of movement or motion of the electronic device using the sensor circuitry,
cause the processor to acquire location information of the electronic device using the location collection circuitry and time information on time when the location information is collected,
acquire first pattern information by analyzing the at least one of movement or motion of the electronic device,
determine, from pre-stored pattern information in the memory, second pattern information corresponding to the acquired location information and time information of the electronic device, and
transmit, through the wireless communication circuitry, a notification including at least one of the first pattern information, the acquired location information and the acquired time information to a designated external electronic device, when the first pattern information does not correspond with the second pattern information.

2. The electronic device of claim 1,
wherein the instructions cause the processor to operate the location collection circuitry with low power consumption in a predetermined condition, and
the predetermined condition includes at least one of whether the electronic device is located in a specific strongpoint, whether the electronic device is in a stop state, or whether a difference between a time when the location information is previously collected and a current time is included in a predetermined value.

3. The electronic device of claim 2, wherein the instructions cause the processor to operate the location collection circuitry with low power consumption for a time when the electronic device is located at the specific strongpoint if a current location of the electronic device is the specific strongpoint, to operate the location collection circuitry with the low power consumption if the electronic device is determined to be in a stop state and the stop state is maintained for a predetermined time, and to operate the location collection circuitry with the low power consumption through reuse of the previous location information if a difference between the time when the location information is previously collected and the current time is included in the predetermined value.

4. The electronic device of claim 2, wherein the location collection circuitry comprises a first location collection circuitry and a second location collection circuitry,
wherein the instructions cause the processor to request the location information of the electronic device from the first location collection circuitry, and to request the location information of the electronic device from the second location collection circuitry if the collected location information exceeds a predetermined range.

5. The electronic device of claim 4, wherein power consumption of the first location collection circuitry is smaller than power consumption of the second location collection circuitry.

6. A method for providing a notification of an electronic device, the method comprising:
collecting at least one of movement or motion of the electronic device;
acquiring location information of the electronic device and time information on time when the location information is collected;
acquiring first pattern information by analyzing the at least one of movement or motion of the electronic device;
determining, from pre-stored pattern information, second pattern information corresponding to the acquired location information and time information of the electronic device; and
transmitting a notification including at least one of the first pattern information, the acquired location information and the acquired time information to a designated external electronic device, when the first pattern information does not correspond with the second pattern information.

7. The method of claim 6, further comprising collecting the location information with low power consumption if the analyzed pattern satisfies a predetermined condition,
wherein the predetermined condition includes at least one of whether the electronic device is located in a specific strongpoint, whether the electronic device is in a stop state, or whether a difference between a time when the location information is previously collected and a current time is included in a predetermined value.

8. The method of claim 7, wherein collecting the location information with the low power consumption comprises at least one of:
collecting the location information with the low power consumption for a time when the electronic device is located at the specific strongpoint if a current location of the electronic device is the specific strongpoint;
determining whether the electronic device is in a stop state, and collecting the location information with the low power consumption if the stop state is maintained for a predetermined time; or
collecting the location information with the low power consumption through reuse of the previous location information if a difference between the time when the location information is previously collected and the current time is included in the predetermined value.

9. The method of claim 7, wherein collecting the location information with the low power consumption comprises:
requesting the location information of the electronic device from a first location collection circuitry; and requesting the location information of the electronic device from a second location collection circuitry if the collected location information exceeds a predetermined range.

10. The method of claim 9, wherein power consumption of the first location collection circuitry is smaller than power consumption of the second location collection circuitry.

* * * * *